(12) United States Patent
Daly

(10) Patent No.: US 8,485,181 B2
(45) Date of Patent: *Jul. 16, 2013

(54) METHOD AND SYSTEM FOR CONTROLLING BREATHING

(75) Inventor: Robert W. Daly, Providence, RI (US)

(73) Assignee: The Periodic Breathing Foundation, LLC, East Providence, RI (US)

(*) Notice: Subject to any disclaimer, the term of this patent is extended or adjusted under 35 U.S.C. 154(b) by 150 days.

This patent is subject to a terminal disclaimer.

(21) Appl. No.: 13/041,783

(22) Filed: Mar. 7, 2011

(65) Prior Publication Data

US 2011/0186050 A1 Aug. 4, 2011

Related U.S. Application Data

(62) Division of application No. 11/405,948, filed on Apr. 17, 2006, now Pat. No. 7,900,626.

(51) Int. Cl.
*A61M 16/00* (2006.01)
(52) U.S. Cl.
USPC . 128/204.18; 128/911; 128/914; 128/205.25; 128/206.15
(58) Field of Classification Search
USPC ............ 128/201.28, 204.18, 204.21–204.23, 128/205.12, 205.19, 205.24, 205.28; 600/529, 600/538
See application file for complete search history.

(56) References Cited

U.S. PATENT DOCUMENTS

| 2,809,633 A | 10/1957 | Swearingen et al. |
| 3,357,426 A | 12/1967 | Cohen |
| 3,697,847 A | 10/1972 | Rygiol |
| 2,291,581 A | 7/1974 | Schulze |
| 4,112,983 A | 9/1978 | Oderbolz et al. |
| 4,188,946 A | 2/1980 | Watson et al. |
| 4,265,235 A | 5/1981 | Fukunaga |
| 4,467,799 A | 8/1984 | Steinberg |
| 4,648,398 A | 3/1987 | Agdanowski et al. |
| 5,320,093 A | 6/1994 | Raemer |

(Continued)

FOREIGN PATENT DOCUMENTS

| EP | 0861672 A1 | 9/1998 |
| FR | 1555589 A | 1/1969 |

(Continued)

OTHER PUBLICATIONS

"Chin Strap Comparison." www.cpapman.com/chnstraps.html. (2007).

(Continued)

*Primary Examiner* — Justine Yu
*Assistant Examiner* — Valerie L Skorupa
(74) *Attorney, Agent, or Firm* — Barlow, Josephs & Holmes, Ltd.

(57) ABSTRACT

The present invention relates to a method and a system for controlling breathing of a patient. A system for controlling breathing of a patient includes a respiratory conduit. The respiratory conduit is configured to be coupled to a patient interface device and is further configured to be coupled to a pressurized air generating device. The respiratory conduit includes at least two air flow control devices, positioned between the patient interface device and the pressurized air generating device. The respiratory conduit includes at least two volumes, wherein one volume is positioned between a first air flow control device and a second air flow control device and another volume is positioned between a second air flow control device and a third air flow control device.

20 Claims, 16 Drawing Sheets

U.S. PATENT DOCUMENTS

| | | | |
|---|---|---|---|
| 5,540,219 A | 7/1996 | Mechlenburg et al. | |
| 5,540,223 A | 7/1996 | Starr et al. | |
| 5,647,345 A | 7/1997 | Saul | |
| 5,676,133 A | 10/1997 | Hickle et al. | |
| 5,755,225 A | 5/1998 | Hutson | |
| 5,794,615 A | 8/1998 | Estes | |
| 5,901,704 A | 5/1999 | Estes et al. | |
| 5,918,598 A | 7/1999 | Belfer et al. | |
| 6,003,511 A | 12/1999 | Fukunaga et al. | |
| 6,009,871 A | 1/2000 | Kiske et al. | |
| 6,196,223 B1 | 3/2001 | Belfer et al. | |
| 6,227,196 B1 | 5/2001 | Jaffe et al. | |
| 6,298,848 B1 | 10/2001 | Skog | |
| 6,306,098 B1 | 10/2001 | Orr et al. | |
| 6,318,362 B1 | 11/2001 | Johnson | |
| 6,341,606 B1 | 1/2002 | Bordewick et al. | |
| 6,349,721 B1 | 2/2002 | Grilliot et al. | |
| 6,354,292 B1 | 3/2002 | Fisher | |
| 6,363,933 B1 | 4/2002 | Berthon-Jones | |
| 6,367,474 B1 | 4/2002 | Berthon-Jones et al. | |
| 6,439,231 B1 | 8/2002 | Fukunaga et al. | |
| 6,467,477 B1 | 10/2002 | Frank et al. | |
| 6,494,206 B1 | 12/2002 | Bergamaschi et al. | |
| 6,584,977 B1 | 7/2003 | Serowski | |
| 6,591,835 B1 | 7/2003 | Blanch | |
| 6,599,252 B2 | 7/2003 | Starr | |
| 6,609,517 B1 | 8/2003 | Estes et al. | |
| 6,612,308 B2 | 9/2003 | Fisher et al. | |
| 6,615,831 B1 | 9/2003 | Tuitt et al. | |
| 6,622,725 B1* | 9/2003 | Fisher et al. | 128/204.21 |
| 6,629,527 B1 | 10/2003 | Estes et al. | |
| 6,640,806 B2 | 11/2003 | Yurko | |
| 6,752,150 B1* | 6/2004 | Remmers et al. | 128/204.18 |
| 6,752,151 B2 | 6/2004 | Hill | |
| 6,799,570 B2 | 10/2004 | Fisher et al. | |
| 6,851,429 B2 | 2/2005 | Bishop | |
| 6,908,438 B2 | 6/2005 | Orr et al. | |
| 6,948,499 B2 | 9/2005 | Griesbach, III et al. | |
| 6,951,217 B2 | 10/2005 | Berthon-Jones | |
| 7,017,577 B2 | 3/2006 | Matich | |
| 7,073,501 B2 | 7/2006 | Remmers et al. | |
| 7,077,138 B2 | 7/2006 | Bateman et al. | |
| 7,810,497 B2* | 10/2010 | Pittman et al. | 128/204.23 |
| 8,074,646 B2* | 12/2011 | Daly | 128/204.18 |
| 2001/0035182 A1 | 11/2001 | Rubin et al. | |
| 2001/0054422 A1 | 12/2001 | Smith et al. | |
| 2002/0059933 A1 | 5/2002 | Jaffe et al. | |
| 2002/0185129 A1 | 12/2002 | Fisher et al. | |
| 2003/0145855 A1 | 8/2003 | Fuhrman et al. | |
| 2003/0217746 A1 | 11/2003 | Gradon et al. | |
| 2004/0016433 A1 | 1/2004 | Estes et al. | |
| 2004/0035422 A1 | 2/2004 | Truitt et al. | |
| 2004/0059239 A1* | 3/2004 | Jaffe et al. | 600/529 |
| 2004/0144383 A1 | 7/2004 | Thomas et al. | |
| 2004/0206354 A1 | 10/2004 | Fisher et al. | |
| 2005/0015036 A1 | 1/2005 | Lutri et al. | |
| 2005/0066976 A1 | 3/2005 | Wondka | |
| 2005/0247316 A1* | 11/2005 | Orr | 128/205.12 |
| 2006/0096598 A1 | 5/2006 | Ho et al. | |

FOREIGN PATENT DOCUMENTS

| | | |
|---|---|---|
| FR | 2827778 A1 | 1/2003 |
| WO | 9710869 A1 | 3/1997 |
| WO | 9834683 A1 | 8/1998 |
| WO | 9952581 A1 | 10/1999 |
| WO | 0045882 A1 | 8/2000 |
| WO | 2007130067 A1 | 11/2007 |

OTHER PUBLICATIONS

"Reusable Silicone Rubber Seal Accessory Attachment for the Hans Budolph 7500 & 7600 Series Oro-Nasal Masks Improves Seating in the Nose Area of the Mask." Sensa Seal™ User Application Instructions. (2004).

Kirkness et al. "Nasal Airflow Dynamics: Mechanism and Reponse Assocaited with an External Dilator Strip." Eur. Resp. J. 15(2000):929-936.

Lorenzi-Filho et al. "Effects of Inhaled Carbon Dioxide and Oxygen on Cheyne-Stokes Respiration in Patients with Heart Failure." Am. J. Resp. Crit. Care Med. 159(1999):1490-1498.

Masumi et al. "Effect of Jaw Position and Posture on Forced Inspiratory Airflow in Normal Subjects and Patients with Obstructive Sleep Apnea." Chest. 109(1996):1484-1489.

Vesely et al. "A Simple, Effective Method for Controlling End Tidal PC02, for MRI Mapping of Cerebrovascular Reactivity." Isocapnia Res. Lab. Accessed Jan. 31, 20006, upon information and belief, this refrence was first published in 2000. www.isocapnis.com/Fine%20%Control%%20of%20PCO2%20and%20pO2.tm.

Vesely et al. "Isocapnic Hypernoea Accelerates Recovery from Isoflurance Anaesthesia." Brit. J. Anaesthesia. 91.6 (2003):787-792.

* cited by examiner

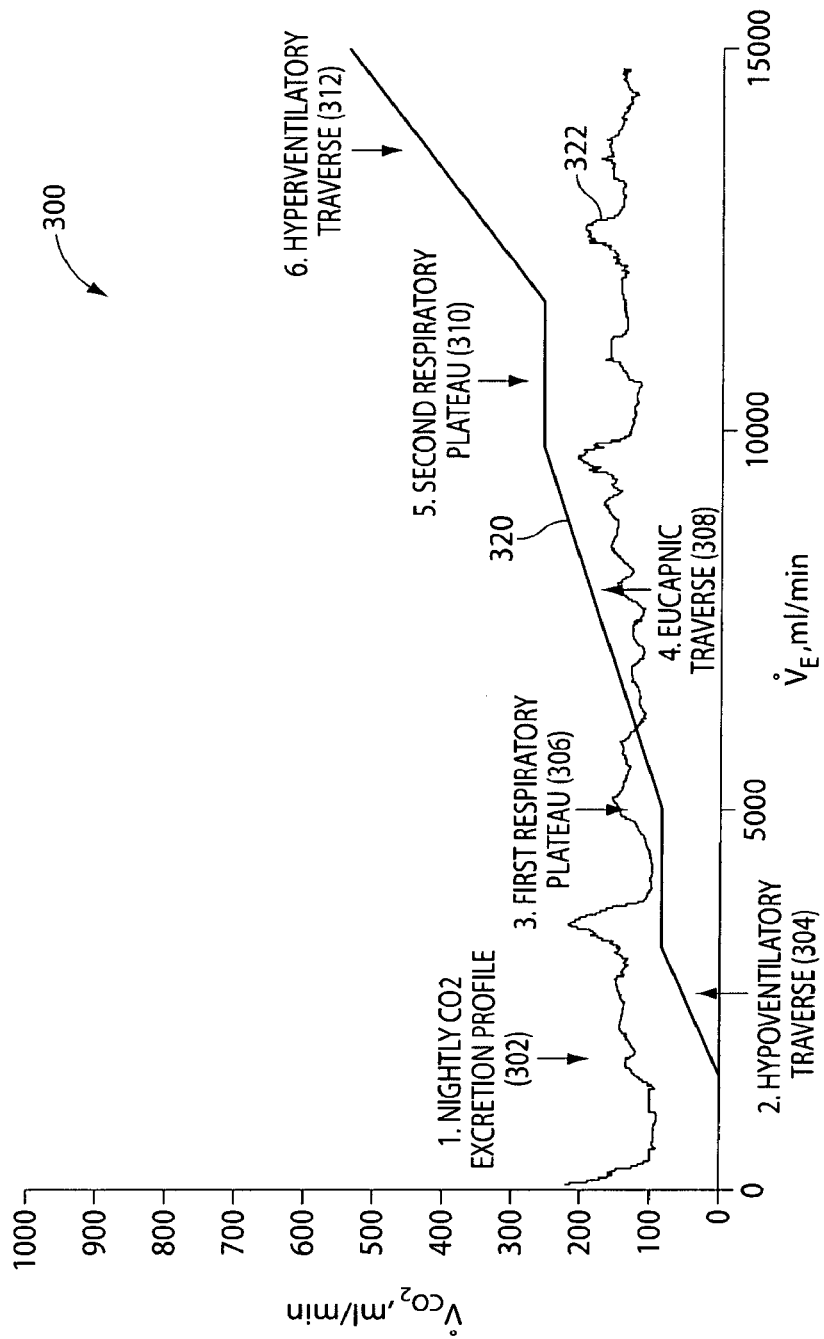

METHOD AND SYSTEM FOR CONTROLLING BREATHING

CROSS-REFERENCE TO RELATED APPLICATIONS

This application is a divisional of and claims priority to U.S. patent application Ser. No. 11/405,948, filed Apr. 17, 2006, entitled Method and System for Controlling Breathing, which is incorporated by reference herein in its entirety.

BACKGROUND OF THE INVENTION

1. Field of the Invention

The present invention relates generally to treatment of breathing disorders. In particular, the present invention relates to systems and methods for controlling breathing of a patient by maintaining specific levels of carbon dioxide ("$CO_2$") dissolved in the patient's arterial blood.

2. Background of the Invention

Sleep-disordered breathing ("SDB") includes all syndromes that pose breathing difficulties during sleep. These include obstructive sleep apnea ("OSA"), mixed sleep apnea ("MSA"), central sleep apnea ("CSA"), Cheyne-Stokes respiration ("CSR"), and others. Some form of SDB occurs in approximately 3-5% of the U.S. population.

While anatomical problems such as obesity or an abnormally narrow upper airway may be a cause of some SDB, neurological difficulties in controlling levels of blood gases, such as $CO_2$ and oxygen ("$O_2$"), are increasingly being recognized as important contributors to the disease. This is especially true of the "central" syndromes, MSA, CSA and CSR, which may account for as much as 20% of all SDB. Changes in the neurological system that controls the blood gases often produce unsteady respiratory patterns that cause arousals from sleep. These changes are accompanied by severe spikes in blood pressure and release of stress hormones that can cause long-term damage to a number of organ systems. Additionally, some SDB syndromes involve abnormal overall levels of blood gases. For example, low levels of dissolved $CO_2$ in arterial blood are frequently encountered, which represents a clinical problem. Thus, there is a need to stabilize respiration and establish appropriate blood gas levels by restoring normal control of blood gases when treating SDB.

SUMMARY OF THE INVENTION

The present invention relates to systems and methods for controlling breathing of a patient by maintaining specified levels of $CO_2$ in arterial blood. The systems and methods can be used to rectify inappropriate levels of both $CO_2$ and $O_2$ in arterial blood. The system includes a respiratory conduit. The respiratory conduit is configured to be coupled to a patient interface device that is coupled to a breathing airway, e.g., nose, mouth or both, of the patient. The respiratory conduit is configured to be coupled to a pressurized air generating device. The respiratory conduit includes at least two air flow control devices, positioned between the patient interface device and the pressurized air generating device. The respiratory conduit includes at least two volumes, wherein one volume is positioned between a first air flow control device and a second air flow control device and another volume is positioned between a second air flow control device and a third air flow control device. Rates of flow of a gas through the first air flow control device and the second air flow control device are calculated based on an expected rate of production of the gas by the patient, expected respiration rate of the patient, expected depth of respiration by the patient, and an expected concentration of the gas in the air expired by the patient.

In an alternate configuration, the system includes a respiratory conduit configured to be coupled to a patient interface device. The respiratory conduit is also configured to be coupled to a pressurized air supply device, wherein the pressurized air supply device supplies air to the patient. The respiratory conduit includes a first valve located adjacent the patient interface device. The first valve includes a first opening configured to control an escape of gas. The conduit also includes a second valve including a second opening configured to control an escape of gas and a first volume connector coupled to the first valve and the second valve. The first volume connector is configured to contain a mixture of air as supplied by the pressurized air supply device and gas as generated by the patient. The conduit includes a third valve having a third fixed opening configured to control an escape of air and a second volume connector coupled to the second valve and the third valve. The second volume connector is configured to contain a mixture of air as supplied by the pressurized air supply device and gas as generated by the patient. The conduit includes a third connector coupled to the third valve and the air supply device. In an example, the amount of gas allowed to escape from each of the three valves is determined by sizes of the valves and two volume connectors, pressure at which the pressurized air supply device operates, respiratory parameters of the patient (e.g., depth and frequency of breathing), production of gas by the patient per unit of time, and concentration of the gas in the patient's arterial blood.

In one example, the system includes a respiratory conduit configured to be coupled to a patient interface device and to a pressurized air supply device. The pressurized air supply device supplies air to the patient. The respiratory conduit includes a first valve located adjacent to the patient interface device that includes a first opening configured to control escape of the gas during the breathing process, a second valve that includes a second opening configured to control escape of gas during the breathing process; a first volume connector connecting the first valve and the second valve and configured to control supply of gas to the patient during the breathing process; a third valve that includes a third opening configured to control escape of gas during the breathing process; a second volume connector connecting the second valve and the third valve and configured to control supply of gas to the patient during the breathing process; a third connector connecting the third valve and the air supply device. The volume of expired gas that is re-breathed (inhaled) by the patient is continuously adjusted based on an amount of gas allowed to escape from the valves and an amount of gas contained in the volume connectors.

In another example, air is supplied to the patient using a patient interface device coupled to an air supply device using a respiratory conduit that includes multiple controllable openings and volume connectors positioned along the length of the respiratory conduit. The method includes determining a rate of production of gas generated by the patient. In an example, the determining also includes measuring the amount of air exhaled by the patient as well as the concentration of gas in such air. Further, the determining can include calculating initial configuration of sizes of multiple controllable openings and volumes using a simulation or an estimation based on variables such as patient's age, gender, body mass, etc. The method further includes measuring a rate of flow and a concentration of gas at each of the multiple controllable openings; adjusting the sizes of the multiple controllable openings based on the measuring; and adjusting the sizes of the multiple volume connectors based on at least one of the determining and the measuring. The air supplied to the patient includes a mixture of air supplied by the air supply device and a gas generated by the patient.

An apparatus for controlling flow of $CO_2$ to a patient during breathing. The apparatus includes a $CO_2$ mixing device coupled to the patient interface device. The $CO_2$ mixing device is configured to be coupled to the pressurized gas device. The $CO_2$ mixing device includes multiple ventilation orifices interchangeably connected with multiple dead spaces, wherein the multiple ventilation orifices control supply of $CO_2$ to the patient and volume of $CO_2$ in the multiple dead spaces. The $CO_2$ mixing device also includes a means for measuring airflow through each of the multiple ventilation orifices; a means of detecting a concentration of $CO_2$ in the measured airflow; a means of adjusting airflow through each of the multiple ventilation orifices based on the detection of the content of $CO_2$; and a means of adjusting sizes of the multiple dead spaces based on the detection of the concentration of $CO_2$ and the adjusting of the airflow through each of the multiple ventilation orifices.

A method for controlling flow of $CO_2$ to a patient during breathing is carried out as follows. The patient interface device is coupled to a $CO_2$ mixing device, which is coupled to air supply device; and the $CO_2$ mixing device includes multiple ventilation orifices interchangeably connected with multiple dead spaces, wherein the multiple ventilation orifices control supply of $CO_2$ to the patient and volume of $CO_2$ in the multiple dead spaces. The method includes measuring airflow through each of the multiple ventilation orifices; detecting a content of $CO_2$ in the measured airflow; adjusting airflow through each of the multiple ventilation orifices based on the detecting of the concentration of $CO_2$; and adjusting sizes of the multiple dead spaces based on the detection of the concentration of $CO_2$ and the adjusting of the airflow through each of the multiple ventilation orifices.

Further features and advantages of the invention, as well as structure and operation of various embodiments of the invention, are disclosed in detail below will reference to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 3 is an exemplary graphical representation of a relationship between ventilation (i.e., the total volume of air exhaled and inhaled by the patient per minute) and $CO_2$ excretion by the patient using systems and methods for controlling breathing of a patient, according to the present invention, along with a tracing representing a rate of $CO_2$ production by the patient during a night.

DETAILED DESCRIPTION

Of the two blood gases, carbon dioxide ("$CO_2$") and oxygen ("$O_2$"), problems with neurological control of breathing during sleep are related to control of $CO_2$ than $O_2$. $CO_2$ is dissolved in blood, and together with bicarbonate ions determines blood pH. Excessive $CO_2$ causes the blood to become acidic, while a deficit in $CO_2$ will cause the blood to be alkaline. Since proteins need a stable pH environment in which to function, the $CO_2$ levels should be controlled within a narrow range that will yield a blood pH of about 7.4. This is accomplished by close matching of $CO_2$ excretion via the lungs to the endogenous $CO_2$ production that is the product of cellular metabolism.

Figure 7:
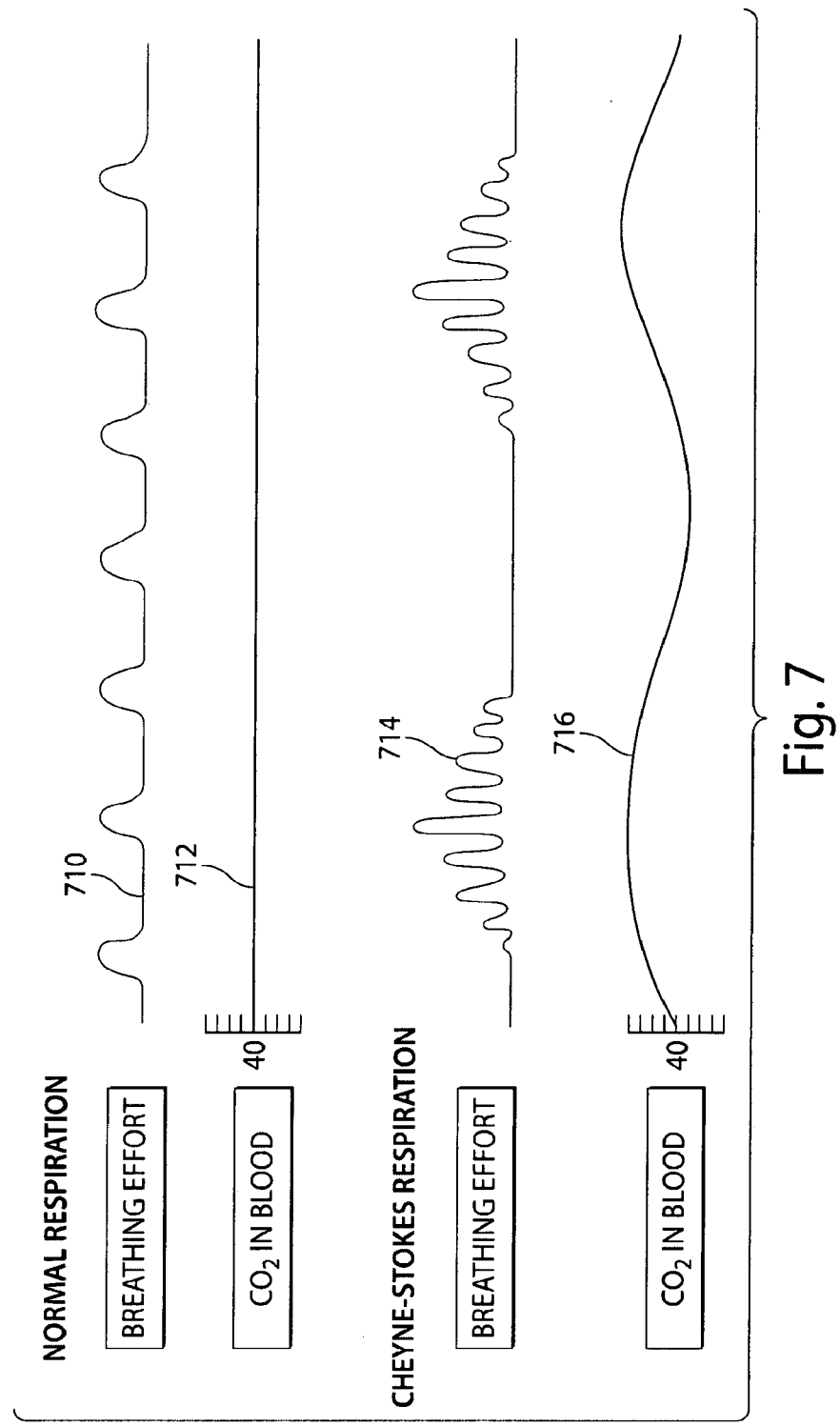
FIG. 7 is a graphical representation of a comparison between normal respiration and Cheyne-Stokes respiration.

FIG. 7 illustrates normal respiration and Cheyne-Stokes respiration plots along with corresponding $CO_2$ blood levels plots. During normal respiration, the breathing effort of a patient is steady, as shown by the plot 710. This corresponds to steady arterial $CO_2$ blood levels, shown in plot 712. A typical normal partial pressure of dissolved $CO_2$ in arterial blood is 40 mm Hg and $O_2$ pressure is approximately 105 mm Hg. During Cheyne-Stokes respiration, the breathing effort is erratic, as illustrated by the waxing/waning plot 714. A corresponding plot 716 shows the associated variable blood $CO_2$ levels during Cheyne-Stokes respiration.

A sensitive and finely tuned system detects blood $CO_2$ levels via a number of sensors, or chemoreceptors located within the vasculature and the brain of the patient. Nerve signaling from these sensors is processed by respiratory control centers in the brain, which send appropriate breathing pattern commands to the respiratory muscles including those of the diaphragm, chest and breathing airway. The goal of the system is to match the excretion of $CO_2$ with the production of $CO_2$ by varying the rate of respiration (both the depth and frequency of breathing). In healthy individuals, this system is accurate and steady. It is able to respond quickly to changes in $CO_2$ production and maintain blood $CO_2$ levels within a narrow range. Like many homeostatic mechanisms in the body, control of blood gases is accomplished by a closed-loop negative feedback control system.

When the system for controlling blood $CO_2$ becomes disordered, it can lose its ability to maintain steady $CO_2$ levels. It "chases" blood $CO_2$ in an oscillating pattern of "overshoot" and "undershoot", resulting in a characteristic waxing/waning respiratory pattern. CSR is the classic syndrome associated with this disordered respiratory patterning and it is common in the setting of a heart failure. FIG. 7 illustrates that normal breathing is accompanied by stable $CO_2$ levels in arterial blood while CSR exhibits oscillating breathing patterns due to unstable $CO_2$ levels.

Since the waxing/waning respiratory drive associated with poor control of blood gases applies also to control of the muscles holding the airway open, cyclic airway collapse during the waning epoch of respiratory drive is often a feature of these syndromes. In fact, pure waxing/waning respiratory patterns not associated with at least intermittent airway collapse are relatively rare and MSA may be the dominant expression of respiratory instability. MSA may present as an extremely regular and predictable pattern of obstructive events associated with reduced respiratory effort but it may also present as a chaotic mixture of events of different kinds (e.g. obstructive apneas, central apneas, hypopneas) with no visually discernable pattern.

For several decades it has been possible to describe the necessary conditions for respiratory stability in mathematical terms. The analytical framework is identical to that used in classical process control theory for predicting the stability of a closed-loop negative feedback control system. While these systems are able stably to control very complex and sensitive processes if correctly tuned, certain categories of problems are known to cause instability and oscillating control that render the process useless or worse. In general, these problems are caused by an excessive sensitivity or "closed-loop gain" in the control loop and timing problems, where an excessive time delay is encountered in measuring the results of the process and taking the appropriate corrective action. These are the same problems that sufferers from unstable sleeping respiration often exhibit.

It is well-established that the underlying cause of instability in the chemical control of respiration is usually excessive gain or sensitivity of one of the blood gas sensors, namely the peripheral chemoreceptor. The peripheral chemoreceptor is located within the carotid artery and directly samples arterial blood for oxygen and $CO_2$ content. The chemoreceptor is sensing the concentration of $H^+$ ions in the blood, which is a proxy for $CO_2$ content in the arterial blood over a short period of time. The sensing becomes disordered and sends signals to the respiratory centers in the brain that tend to overestimate changes in blood gases, specifically, $CO_2$. Even though the cause of the disordered sensing is unknown, it is common in various diseases, e.g., heart failure. It is difficult to correct the above disordered sensing using current medical technology. Further, problems with blood circulation prolong the time delay in reporting changes in blood gases, which adds to the problem of instability in the patient's respiratory control loop.

Given that increased closed-loop gain in the respiratory control feedback loop resulting in unstable respiration is usually due either to excessively sensitive $CO_2$ sensors or impaired blood circulation, a number of therapeutic strategies have been attempted. Most existing therapies have various drawbacks.

Current therapeutic methods for restoring sleeping respiratory instability have the following problems:
1. They are complicated.
2. They are costly.
3. They are inefficient in that they may reduce one aspect of the closed-loop respiratory control gain while increasing its other aspects. Further, they may fail to reliably reinstate conditions for stability.
4. They fail to enable a clinician to specify a target blood $CO_2$ range to be maintained during therapy where patients are currently hypocapnic.
5. They reduce an amount of oxygen available for breathing, necessitating an addition of supplemental oxygen in order to restore normal level of blood oxygen.
6. They fail rapidly to excrete $CO_2$ under extraordinary circumstances, such as, after a prolonged obstructive apnea event.
7. They fail to respond immediately on a breath-by-breath basis to unstable respiratory patterns and rely on multi-breath pattern-recognition algorithms.
8. They relay on a single fixed estimate of respiratory requirements during the course of treatment and are not configured to adapt to variation in respiratory requirements.
9. They rely on expensive electronic equipment.

Current methods are also unable to permit modeling of the relationship between the rate ventilation of the patient and the rate of $CO_2$ excretion in a non-linear fashion, including imposition of multiple distinct steps that permit "clamping" of respiration by maintaining $CO_2$ excretion within a defined range under most conditions.

The system and method capable of controlling breathing of a patient by maintaining certain levels of $CO_2$ in the patient's blood, while maintaining or improving blood oxygenation, described herein provide a solution to these problems.

The present invention also provides a way to substantially eliminate "deadspace gain". This issue is present in some conventional breathing systems.

Unstable breathing patterns consist of alternating hyperventilation and hypoventilation or apnea. During hyperventilation, there is rapid "blow-off" of $CO_2$ that causes a steep drop in arterial $CO_2$ that initiates an epoch of hypoventilation or even apnea when the arterial blood reaches the peripheral chemoreceptor and the brain detects an abnormally low level of blood $CO_2$. During the hypoventilation, $CO_2$ accumulates rapidly and again initiates an epoch of hyperventilation. This pattern can be repeated indefinitely.

Ideally, the lungs should be made to be less efficient during hyperventilation in order to resist the $CO_2$ blow-off. One of the ways to do this, is to make the patient inhale a high percentage of $CO_2$ in inspired air, which will interfere with gas exchange in the lungs and therefore exhibit excessive excretion of $CO_2$ Likewise, the lungs should be maximally efficient during hypoventilation in order to limit the accumulation of $CO_2$. Thus, inhaled $CO_2$ is optimally zero during hypoventilation. Any design can be characterized in terms of its ability to exert a stabilizing influence by feeding the patient high concentrations of inspired $CO_2$ during hyperventilation and none during hypoventilation.

Figure 13:
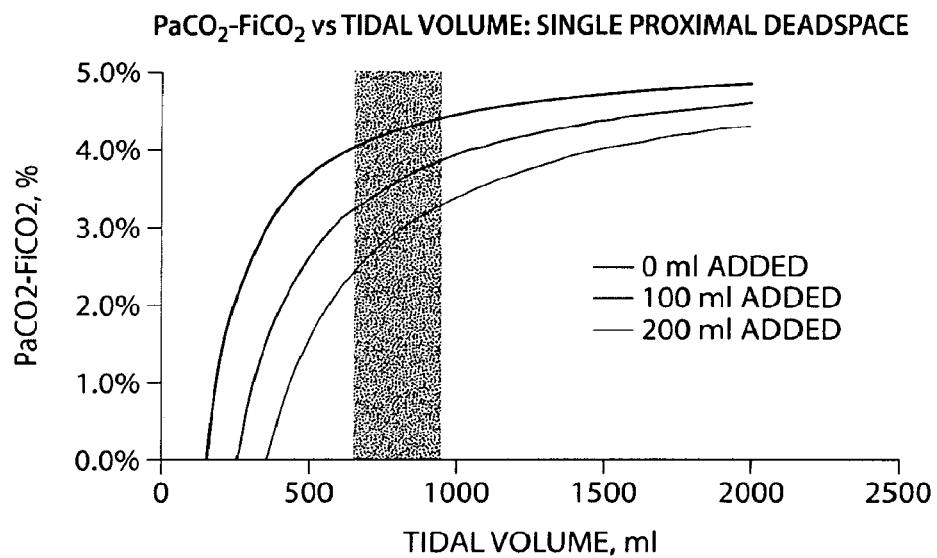
FIGS. 13-15 is a series of tracings indicating deadspace gain in conventional breathing systems.
Figure 14:
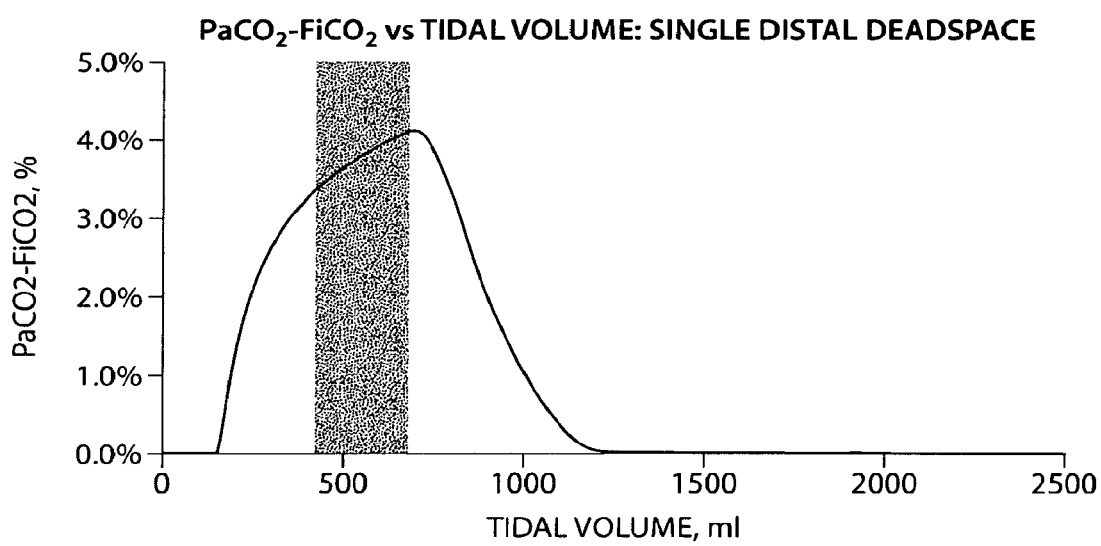
Figure 15:
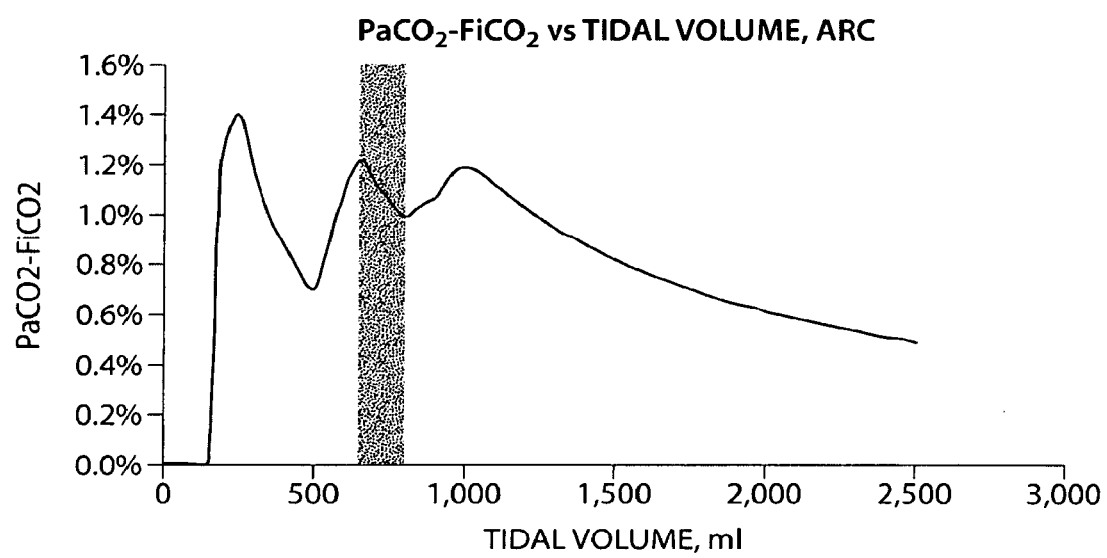

Unfortunately, the conventional deadspace systems tend to do the opposite. As tidal volume increases, the concentration of $CO_2$ in inspired air decreases, thus, actually promoting instability. FIGS. 13-15 illustrate that during normal breathing the deadspace gains of both proximal single deadspace design and distal single deadspace design are quite high. Single proximal deadspace systems interpose a single deadspace volume between a sealed patient interface and a single orifice configured to be large enough to permit flow through the orifice sufficient to wash out all exhaled gases that exceed the volume of the single deadspace. Such devices are then further connected to an air supply device via a typical respiratory conduit. Single distal deadspace systems are configured with a single orifice substantially on or near the patient interface and with a single conduit comprising the entire deadspace acting as a coupling to the air supply device. The single orifice is configured to permit a certain maximum amount of a gas to be excreted from the device and to cause substantial re-breathing of any additional exhaled gas. High deadspace gain is signified by a steep positive slope of the function in the shaded zone. The shaded zone represents a range of normal breathing while using the device.

Further features and advantages of the invention, as well as the structure and operation of various embodiments of the invention, are described in detail below with reference to the accompanying drawings. The invention is not limited to the specific embodiments described herein. Such embodiments are presented herein for illustrative purposes only. Additional embodiments will be apparent to persons skilled in the relevant art(s) based on the teachings contained herein.

While the present invention is described herein with reference to illustrative embodiments for particular applications, the invention is not limited thereto. Those skilled in the art with access to the teachings provided herein will recognize additional modifications, applications, and embodiments within the scope thereof and additional fields in which the present invention would be of significant utility.

Regulation of Blood Gas Levels

Methods and systems for controlling breathing of a patient are described herein. The methods and systems use a combination of multiple deadspace volumes and valves to control $CO_2$ levels in a patient's blood and, thereby, control breathing of the patient. The device of the therapeutic system controls a relationship between the rate of ventilation (i.e., total minute volume, $\overset{\circ}{V}_E$) and the rate of $CO_2$ excretion ($\overset{\circ}{V}_{CO_2}$) while permitting extensive modeling of this relationship in a non-linear, discontinuous fashion (See, FIG. 3 discussion below). This system allows a clinician to define a level of arterial blood $CO_2$ to be maintained during therapy as well as to place strong limits on both hyperventilation and hypoventilation. Under certain circumstances, the present invention can increase blood oxygenation without the use of supplemental oxygen.

The system provides an interaction between multiple discreet deadspace volumes and multiple ventilation orifices of either fixed (precisely-defined) or variable size, where the volumes and orifices can be organized in a specific pattern. Such interaction offers a possibility of defining a wide spectrum of relationships between the rate of ventilation and the rate of $CO_2$ excretion by the patient when used in conjunction with a ventilatory assist device such as a Continuous Positive Airway Pressure ("CPAP") machine, which is set to a predetermined pressure. In an alternate embodiment, a ventilatory assist device is not used and the same effect is achieved using a simple device into which the patient breathes.

A respiratory conduit, which is placed between a patient interface device (e.g., a sealed CPAP mask) and the CPAP machine (or any other air supply device), has a cylindrical shape. Ventilation orifices are placed in line with the conduit to provide outflow of $CO_2$ that is exhaled by the patient. The lengths of conduit lying between each ventilation orifice represent a distinct deadspace or quasi-deadspace volume. As air containing $CO_2$ is expelled from the patient's lungs into the respiratory conduit, a pressure generated by the CPAP machine causes at least some of the air and $CO_2$ contained in such air to flow out of the various orifices in a specific pattern. The pattern depends on the volume of each one of patient's breaths or tidal volume ($V_T$) and the frequency of breathing, or respiration rate. Each breath consists of an expiratory interval and an inspiratory interval. Once the expiratory interval is over, inspiration commences and most or all of the remaining $CO_2$ in the conduit is re-breathed by the patient. Depending on the volume of each deadspace and the size of each ventilatory orifice, the curve describing a relationship between the rate of ventilation and the rate of $CO_2$ excretion has an arbitrary number of inflection points defining line or curve segments (See, FIG. 3), each with a different slope and length.

The above system permits extensive modeling of the relationship between a patient's breathing (i.e., ventilation) and excretion of $CO_2$. Using conventional computer simulation techniques, the sizes of orifices, volumes, and/or configuration of the two are specified to establish a relationship that serves to return the respiratory control feedback loop to a stable operation. Since during the interval prior to falling asleep, $CO_2$ production may be high relative to the levels anticipated to prevail during sleep, an auxiliary ventilation valve is fitted that permits the patient to increase airflow through the device until comfortably resting in bed.

Figure 1A:
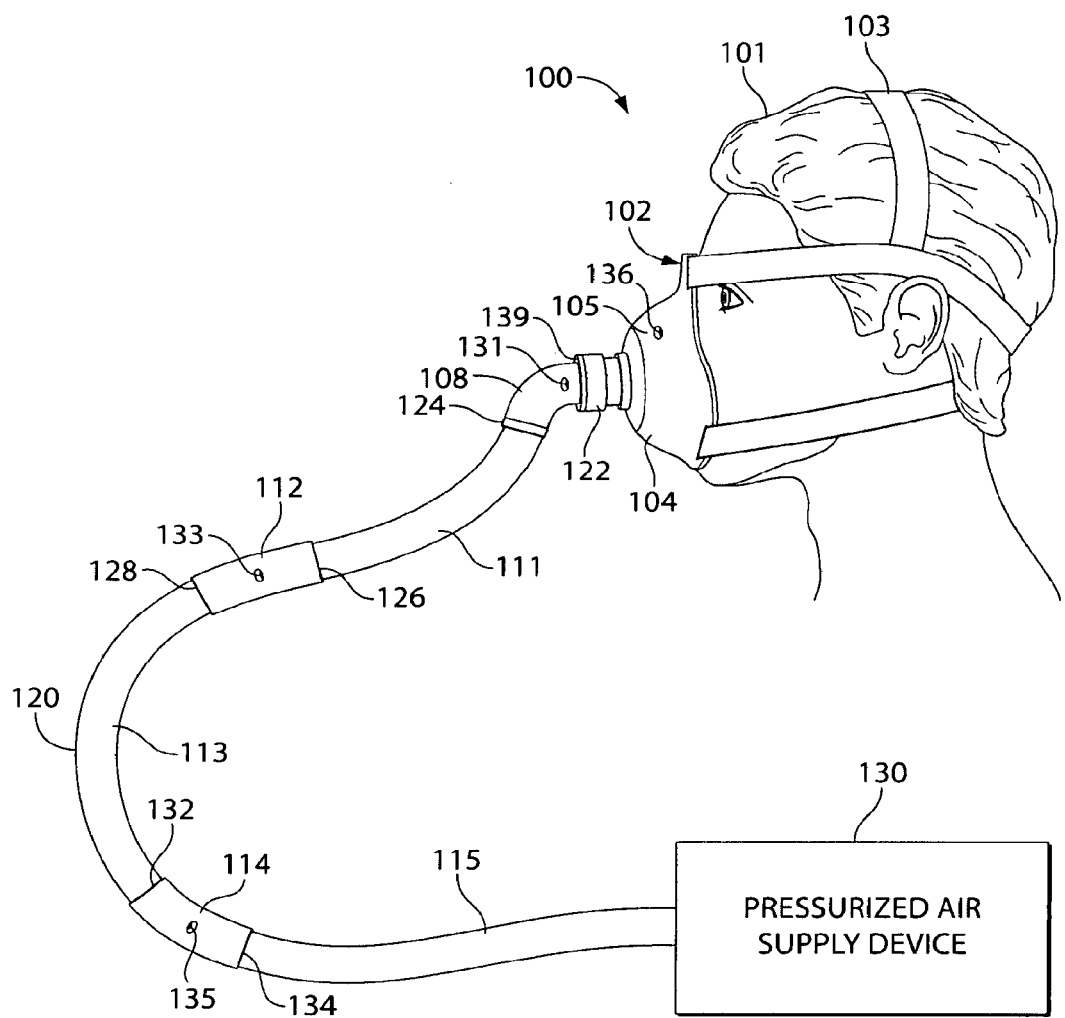
FIG. 1A is an illustration showing an exemplary system for controlling breathing of a patient, according to the present invention.
Figure 1B:
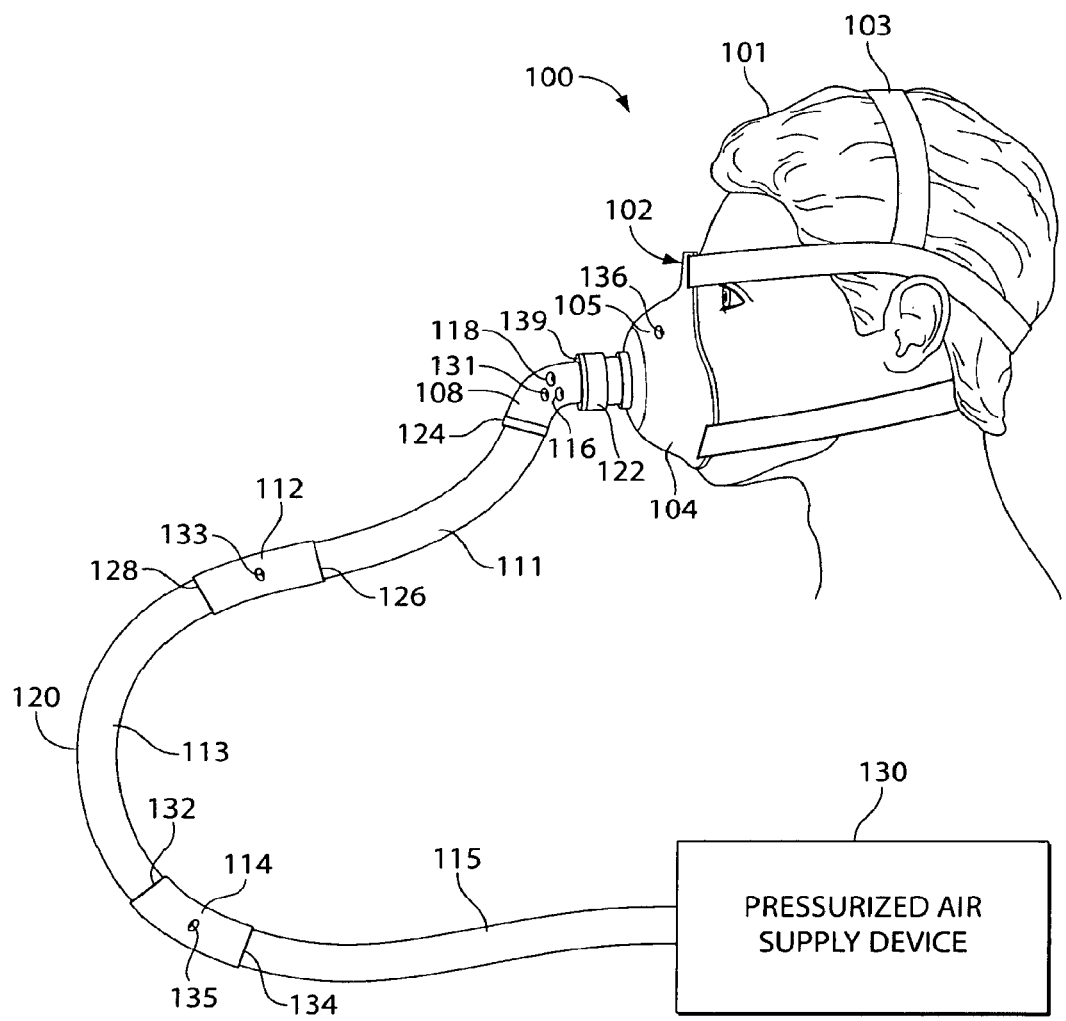
FIG. 1B is another illustration showing an exemplary system for controlling breathing of a patient, according to the present invention.

FIGS. 1A and 1B illustrate an exemplary system 100 for controlling breathing of a patient 101. Referring to FIG. 1A, the system 100 includes a respiratory conduit or a mixing device 120 configured to be coupled to mask and headgear assembly 102 and to a pressurized air supply device or CPAP device 130. The mask and headgear assembly 102 includes multiple straps 103 and a mask 104. The multiple straps 103 secure the mask 104 to the face of patient 101 so that there is a substantially sealed connection between the mask and the patient's breathing airway (e.g., nose or mouth). The sealed interface or connection prevents uncontrolled leakage of air or gases from openings that may occur between the patient's face and the mask. In the exemplary embodiment of FIG. 1A, one or a plurality of straps 103 are placed over upper and lower portions of the patient's head. As understood by one of ordinary skill in the art, other ways of securing the mask 104 to the patient 101 are encompassed herein. A pressurized and/or non-pressurized gaseous substance (including air, gas, etc.) generating device, e.g., the CPAP device 130, can be used with the therapeutic breathing system.

The mask 104 is a sealed orofacial non-invasive ventilation mask. For example, the mask 104 can be a Mirage NV Full Face Mask with adjustable VELCRO® strap headgear, as manufactured by ResMed Corp., Poway, Calif. A full-face mask can be used to cover both the nose and the mouth. This design eliminates mouth leak, permitting therapy for patients who breathe through the mouth and/or the nose. As can be understood by one of ordinary skill in the art, other types of masks can be used, such as a nasal mask, an oral mask, an orofacial mask, a nasal prong device, an intra-oral device, an endotracheal tube, or any other device.

The mask 104 includes a mask valve 105. The mask valve 105 can be a female Luer fitting that includes an orifice 136 and that attaches to one of the existing Luer ports on the mask 104. The orifice 136 can be drilled, punctured, or created by any other methods. The mask valve 105, through orifice 136, allows escape of gas (e.g., $CO_2$) exhaled by the patient. Alternatively, the mask 104 does not include the mask valve 105. Instead, a first valve 108 is placed on the mixing device 120, substantially adjacent to the mask 104. In one example, the orifice 136 has a fixed size. This design allows a certain volume of air to escape from the mask valve 105 per unit of time. In another example, the orifice 136 has a variable size, which can be altered depending on the amount of air intended to be allowed to escape from the mask valve 105. In one example, the orifice 136 permits air flow of 0.5-6 liters per minute, when the mask is pressurized by the CPAP machine 130 at a specific pressure. This pressure can be equal to the patient's CPAP pressure prescription.

Referring back to FIG. 1A, the mixing device 120 includes a first valve 108, a first volume 111, a second valve 112, a second volume 113, a third valve 114, and a connector volume 115. The first valve 108 includes an orifice 131. The second valve 112 includes an orifice 133. The third valve 114 includes an orifice 135. As can be understood by one having ordinary skill in the relevant art, the mask valve 105 can be the first valve 108. The mask valve 105 can be included or absent from the mask 104. Also, the first valve 108 can be placed on the mask 104 instead of the fitting 139.

As shown in FIG. 1A, a fitting 139 incorporates the first valve 108. The fitting 139 is coupled to the mask 104 and the first volume 111. The second valve 112 is coupled to the first volume 111 and the second volume 113. The third valve 114 is coupled to the second volume 113 and connector volume 115. The connector volume 115 is coupled to the pressurized air/gas generating device 130.

The fitting 139 further includes fittings 122 and 124 through which it is coupled to the mask 104 and first volume 111, respectively. The fittings 122, 124 can be standard type fittings having 22 mm outside diameter ("o.d."). To allow proper connection to the fitting 139, the first volume 111 can be a standard 22 mm inside diameter ("i.d.") respiratory hose.

Further, the fittings 122, 124 can be of a swivel type to permit rotation of the fitting 139 to accommodate various positions and orientations of the mixing device 120 and provide substantially leak proof connection. Otherwise, fitting 139 can be a straight fitting or a bent fitting, for example a fitting with two 22 mm o.d. ends and a 90-degree bend. The first valve 108 provides an air flow of 0.5 to 6 liters per minute when the system 100 is pressurized by the CPAP machine 130 at a given pressure equal to the patient's CPAP pressure prescription. Fittings 126, 128 (coupling second valve 112 to first volume 111 and second volume 113, respectively) and fittings 132, 134 (coupling third valve 114 to second volume 113 and connector volume 115, respectively) can be similar to fittings 122, 124.

The first volume 111 can be a standard 22 mm i.d. respiratory hose and can have an internal volume of 100-400 ml depending on the desired increase in the patients' arterial $CO_2$. The hose can be a conventional hose with rubber cuffs as used with CPAP machines; it can be a corrugated disposable respiratory hose, or it can be any other hose appropriate for connecting mask 104 to a fitting 126.

As stated above, the second valve 112 includes a straight connector incorporating the orifice 133 that can have a fixed size. Alternatively, the orifice 133 has a variable size. This connector can be plastic and have 22 mm o.d. ends suitable for connection to the first volume 111 and second volume 113. Further, the orifice 133 location in the connector is such that it is not obstructed by lying on a surface (e.g., a bed). A groove in the fitting containing the second valve 112 can be created to prevent any obstructions. The orifice 133 permits an airflow of 3-8 liters per minute when it is pressurized by the CPAP machine 130 at a given pressure equal to the patient's CPAP pressure prescription.

The second volume 113 is substantially identical in type to the first volume 111. The second volume 113 can have a total volume of 100-400 ml.

The third valve 114 incorporates the orifice 135, which can be variable or fixed. The third valve 114 can be a straight connector, as shown in FIG. 1A. The connector can be plastic and have 22 mm o.d. ends suitable for connection to the first volume 113 and connector volume 115. The orifice 135 location in the mixing device 120 is such that it is not obstructed by lying on a surface (e.g., a bed). A groove in the fitting containing the third valve 114 can be created to prevent any obstructions. The orifice 135 permits an airflow of 15-30 liters per minute when it is pressurized by the CPAP machine 130 at a given pressure that is equal to the patient's CPAP pressure prescription.

The connector volume 115 can be substantially identical in type to the first volume 111 and second volume 113. The length of the connector volume 115 can be set to accommodate placement of the CPAP machine 130 in relation to the patient 101.

Each one of the orifices 131 (or alternatively 136), 133, and 135 is configured to allow escape of air at a specific rate when the pressurized air supply device 130 is operated at a specific pressure. Depending on the concentration of gas in the air flowing through each of the orifices, the gas will be escaping through each orifice at a specific rate. The orifices can be fixed, variable, or a combination of fixed and variable sized orifices can be used. As can be understood by one having ordinary skill in the art, varying locations and/or numbers of fixed and variable orifices can be used as desired. This allows a predetermined amount of air and gas (depending on the concentration of the gas in such air) to escape from the orifices in case of fixed orifices' sizes or a variable amount of gas to escape from the orifices in case of variable orifices' sizes. Further, in case of variable orifices, their sizes can be manually or dynamically controlled. When orifice sizes are manually controlled, a patient, a clinician, or someone else can control the size of the orifice and, thus, the amount of gas allowed to escape from the orifice. When orifice sizes are automatically controlled, their sizes can be adjusted automatically based on an amount of gas exhaled by the patient, amount of gas escaping from each specific orifice, amount of gas contained in the volume connectors 111 and 113, patient physical parameters (such as blood pressure, body mass, age, etc.) and/or other factors.

The sizes of orifices 131, 133, 135 and three volumes 111, 113, 115 can be preliminary determined using an algorithm based on patient's estimated high and low $\overset{\circ}{V}_{CO_2}$ (rate of production of $CO_2$ in ml per minute) as directly measured during sleep. Alternatively, the patient's estimated high and low $\overset{\circ}{V}_{CO_2}$ can be derived from patient's body mass or any other physiological or demographic variable or combination of variable. The sizes of volumes and orifices are adjusted during a polysomnographic study in a clinic, hospital, laboratory, or any other facility that is equipped with $CO_2$ monitoring equipment. Based on the adjustment, a final combination of orifices and volumes is determined. This combination establishes a first respiratory plateau (See, FIG. 3, segment 308) at or below a value of $\overset{\circ}{V}_{CO_2}$ equal to the minimum estimated $CO_2$ production per minute expected to occur during sleep and a second respiratory plateau (See, FIG. 3, segment 310) at or above a value of $\overset{\circ}{V}_{CO_2}$ equal to the maximum estimated $CO_2$ production per minute expected to occur during sleep.

The respiratory conduit 120 is rotatably coupled to the mask 104 and the CPAP device 130. This arrangement allows the conduit 120 to rotate if the patient turns during sleep. As can be understood by one of ordinary skill in the art, the rotatable connection can be sealed to prevent any leaks during operation of system 100.

Referring to FIG. 1B, the conduit 120 includes an anti-asphyxiation valve 118 and any number of auxiliary valves 116 that can assist a patient during breathing. In the FIG. 1B example, the anti-asphyxiation valve 118 and the auxiliary valve 116 are placed in the fitting 139.

The auxiliary valve 116, when opened, provides a flow of air through the mixing device 120 sufficient to provide substantial washout of the exhaled $CO_2$ from the mixing device 120. In one example, the patient 101 can operate the auxiliary valve 116 in order to provide $CO_2$ washout until patient 101 is resting comfortably. The auxiliary valve 116 can be closed manually by the patient 101 or automatically after a certain period of time elapsed.

The anti-asphyxiation valve 118 opens when the operating pressure of the CPAP machine 130 falls below a predefined value (i.e., CPAP machine 130 fails to provide adequate pressure). When the latter occurs, the anti-asphyxiation valve 118 opens and allows the patient 101 to breathe ambient air through the valve 118. Hence, the valve 118 prevents asphyxiation of the patient in the event of failure of the CPAP machine 130.

Additionally, the mixing device 120 includes a water condensation collection device that collects moisture from the patient's breaths. This prevents undesirable accumulation of moisture within the mixing device 120.

For example, it may be determined that a male patient with a body mass of 100 kg and a CPAP prescription of 15 cm $H_2O$ may require the following configuration of orifices and volumes:

| | |
|---|---|
| Orifice 131 | 3 liters per minute |
| First volume 113 | 350 ml |
| Orifice 133 | 5 liters per minute |
| Second volume 115 | 400 ml |
| Orifice 135 | 22 liters per minute |

Figure 2A:
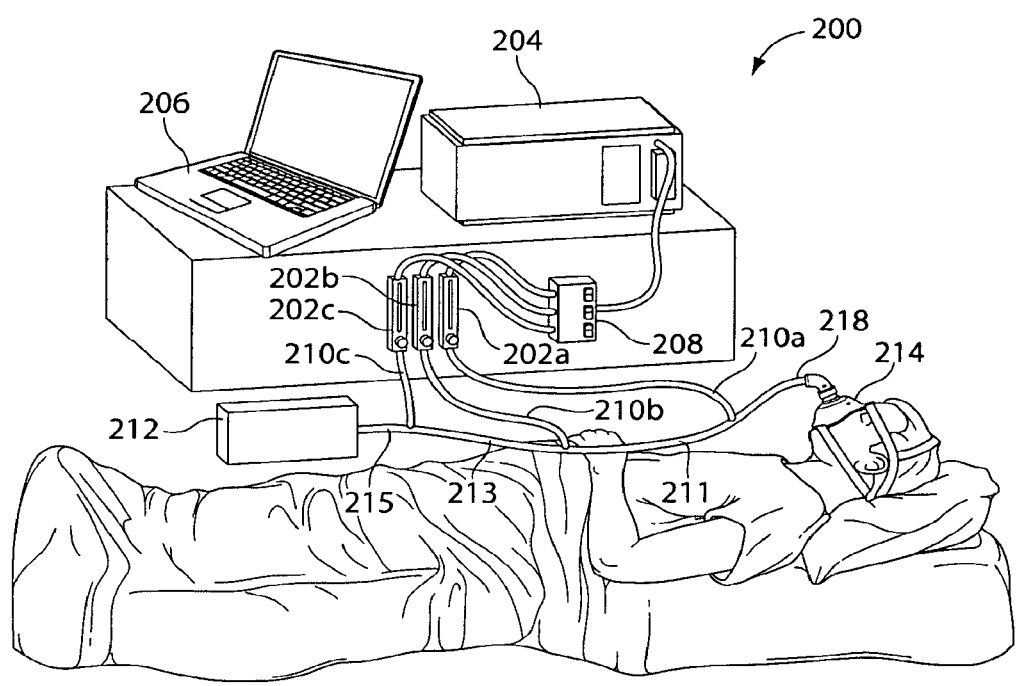
FIG. 2A is an illustration showing exemplary clinical equipment set up using methods and systems for controlling breathing of a patient, according to the present invention.

FIG. 2A illustrates an exemplary set up 200 for a polysomnographic and/or titration study of a patient. The set up 200 includes a $CO_2$ monitor 204, a computing device 206, variable area flow meters 202 (a, b, c) having needle valve controls, a CPAP machine 212, a switchable manifold 208, tubing 210 (a, b, c), a conduit 218, and an orofacial mask 214.

The mask 214 is similar to 104 shown in FIGS. 1A and 1B. The CPAP machine 212 is similar to the CPAP machine 130. Also, the conduit 218 is similar to the mixing device 120. The conduit 218 connects mask 214 and CPAP machine 212. The conduit 218 is also connected to tubing 210 (a, b, c). The conduit 218 includes a first volume 211, a second volume 213, and a connector volume 215, which are similar to the volumes 111, 113, and 115, respectively. The tubing 210a connects orifice 131 (not shown in FIG. 2A) a flow meter 202a. The tubing 210b connects orifice 133 (not shown in FIG. 2A) to a flow meter 202b. The tubing 210c connects orifice 135 (not shown in FIG. 2A) to a flow meter 202c. The tubing 210 (a, b, c) can be ⅜ inch i.d. Tygon tubing. The tubing 210 (a, b, c) can be glued, cemented, or otherwise securely fastened to the orifices 131, 133, 135 and flow meters 202 (a, b, c), respectively.

Figure 2B:
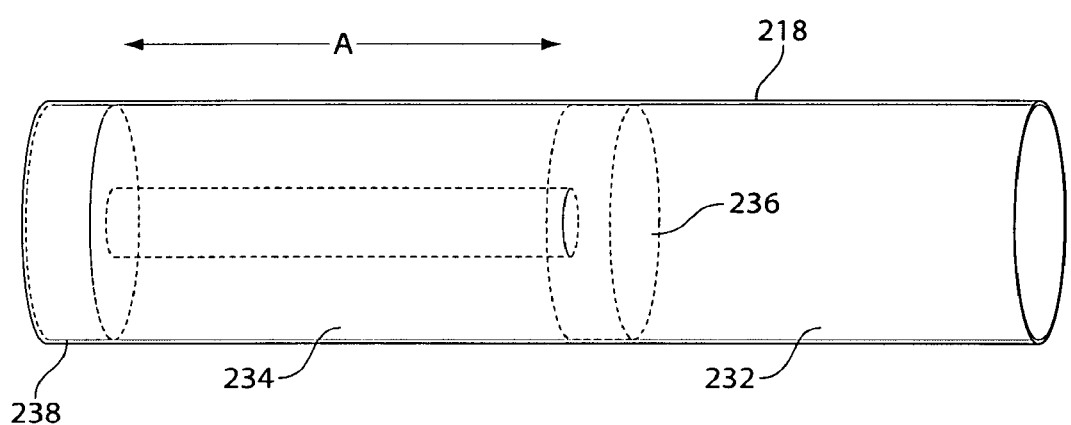
FIG. 2B is an illustration of a portion of breathing conduit shown in FIGS. 1A-2A.

Further, the conduit 218 is configured to vary volumes 213 and 215 using movable pistons or cylinders (shown in FIG. 2B) located inside the volumes 213 and 215. The cylinders can be sealed using o-ring clamps (shown in FIG. 2B). FIG. 2B illustrates a portion of the conduit 218 having a cylinder/piston 236 placed in the conduit's interior 234. The cylinder/piston 236 is able to move back and forth as shown by the bi-directional arrow A. The movement increases or decreases deadspace volume 232. The cylinder/piston 236 is secured by an o-ring clamp 238. This cylinder/piston 236 arrangement can be placed in either or all volumes 211, 213, and 215. The volumes can also include graduation scales (not shown in FIGS. 2A, 2B) to adjust the deadspace volume 232 to a specific value.

Referring back to FIG. 2A, the output sides of the flow meters 202 (a, b, c) are coupled to switchable manifold 208, which allows measurement of $CO_2$ content in the air flowing from any one of or a combination of the variable flow meters 202 (a, b, c) by the monitor 204. The monitor 204 is connected to the computing device 206, which collects the data. The data is used to adjust the rates of airflow through each of the flow meters 202 and the sizes of the volumes, as described with respect to FIGS. 1A, 1B and 3-9.

Method of Treatment and Titration of a Patient

Initially, a nightly $CO_2$ excretory profile of a patient during sleep is determined. This profile is determined by measuring a total amount of $CO_2$ production by the patient during a diagnostic overnight polysomnographic study. Such profile contains information about high, low and mean levels of $CO_2$ production during sleep. Prior to a trial fitting of the device (See, FIGS. 1A-2) on a patient, the collected data along with other patient physiological data and desired therapeutic results are used to generate a simulation model, which provides a best estimate of a configuration of volumes and orifices to be used during treatment. During a subsequent polysomnographic titration study the device is fitted on the patient, an initial CPAP pressure is selected and an actual $CO_2$ flow through each of the orifices is measured at the predetermined air flow rate. The orifice sizes are adjusted (either manually or automatically) so that the $CO_2$ flow through or escape from each orifice equals a desired value depending on an intended relationship to the patient's $CO_2$ excretory profile. The volumes' sizes are also adjusted (whether manually or automatically). This depends on whether patient's mean amount of arterial $CO_2$ diverges from the desired level. The adjustment of sizes can be done by physically substituting volume hoses of known size. Alternatively, a cylinder/piston arrangement (shown in FIG. 2B) can be inserted into each of the volumes to manually or automatically decrease or increase the interior spaces of the volumes based on the obtained data and desired values. In the event that it is necessary to change the starting CPAP pressure, the procedure of measuring and adjusting can be repeated to return to a specific desired result.

At the end of the titration study, a final configuration of CPAP pressure, volumes and airflow through each of orifices is recorded. A custom-built conduit/mixing device (as shown in FIGS. 1A-2B) can be manufactured according to these specifications and dispensed to a patient for use. As can be understood by one having ordinary skill in the art, various configurations of orifices and volumes are possible.

The device and therapeutic system is tailored to each individual patient. Initially, the patient is referred to an appropriate sleep diagnostic facility. In the facility, a clinician orders an evaluation of a patient for possible respiratory instability. Certain modifications and enhancements are optionally made to the usual overnight polysomnographic study, described above. These modifications can include additions of end-tidal $CO_2$ monitoring and calibrated nasal pressure measurement. Alternatively, instead of nasal pressure, another highly accurate means of determining airflow through the patient's nose and mouth can be utilized, including wearing a respiratory mask with an attached flow sensor. The capnography ($CO_2$) waveform (See, FIG. 6) and flow signals are recorded throughout the night and stored in the polysomnographic recording system. As a result of the study, either in real time or a post-study process, a patient's minute $CO_2$ volume ($\overset{\circ}{V}_{CO_2}$) versus time, i.e., a rate of $CO_2$ excretion during sleep, is derived by multiplying the sum of the rates of airflow through the orifices and the airflow meters and the percentage of $CO_2$ in the air, as measured by the end-tidal $CO_2$ monitor. The patient's $CO_2$ excretion profile is determined using a number of commercially available analytic packages, such as DASYlab, manufactured by National Instruments Corporation of Austin, Tex.

The interpreting clinician inspects the evolution of $\overset{\circ}{V}_{CO_2}$ during the course of the night and determines the predicted low, mean, and high $\overset{\circ}{V}_{CO_2}$ targets for which the device should be configured. The clinician also inspects the end-tidal $CO_2$ waveform itself to evaluate the evolution of arterial $CO_2$ and to determine to what degree the patient will require overall $CO_2$ support in order to reach a target mean arterial $CO_2$ level during the night. The clinician then again refers the patient for a titration study using the present invention.

Prior to the titration study, the polysomnographic technician will obtain certain demographic and physical information about the patient in order to establish a starting configuration. For example, age, sex, body mass, arterial $CO_2$ level, estimated CPAP prescription, and actual and target end-tidal $CO_2$ values are collected. This information is then used to make an estimate of a probable optimal configuration of orifices and volumes. Patient's age, sex and body mass are used to derive a probable low, mean, and high value for sleeping $\overset{\circ}{V}_{CO_2}$ based on at least studies of multiple patients. Then, $\overset{\circ}{V}_{CO_2}$ values are used to set target flow rates for the orifices and determine the size of the orifices based on flow rates through each orifice under pressure. The size of the first deadspace volume 111 is estimated based on the desired target end-tidal $CO_2$. Finally, a minimum size for the third orifice 115 is estimated. This permits a washout of any overflow $CO_2$.

After the study is completed, the patient can be provided with a home-use device that is similar to the system 100 shown in FIG. 1. Alternatively, the patient can be scheduled for treatment at a clinic using the system of present invention. The device is capable of the following exemplary functions (i) measuring an airflow through each ventilatory orifice 131, 133, 135 individually (conventional gauges can be used as variable area flowmeters or electronic flowmeters coupled to an input/output device, e.g., a computer, can be used to measure the airflow);

(ii) detecting $CO_2$ content in airstreams stemming from each orifice 131, 133, 135 and transmitting the collected content data to an input/output device, e.g., a computer;

(iii) adjusting airflow through (or escaping from) each of the orifices 131, 133, 135 using valves (the valves can be operated manually or automatically);

(iv) adjusting sizes of the two deadspace volumes by disconnecting and connecting hoses of various lengths (alternatively, variable volume devices can be incorporated, which permit altering the deadspace volumes without changing hoses; the variable volume devices can be nested cylinders sealed with o-rings that can slide in and out); and (v) computing and displaying a rate of flow of $CO_2$ through each of the orifices (this function can be performed by any computing device having an appropriate data acquisition peripheral device running on software, such as DASYLab, which permits acquisition of both the $CO_2$ and flow data channels; a suitable display can be used to permit a clinician to observe flow of $CO_2$ through each orifice as the volumes are adjusted).

Figure 8:
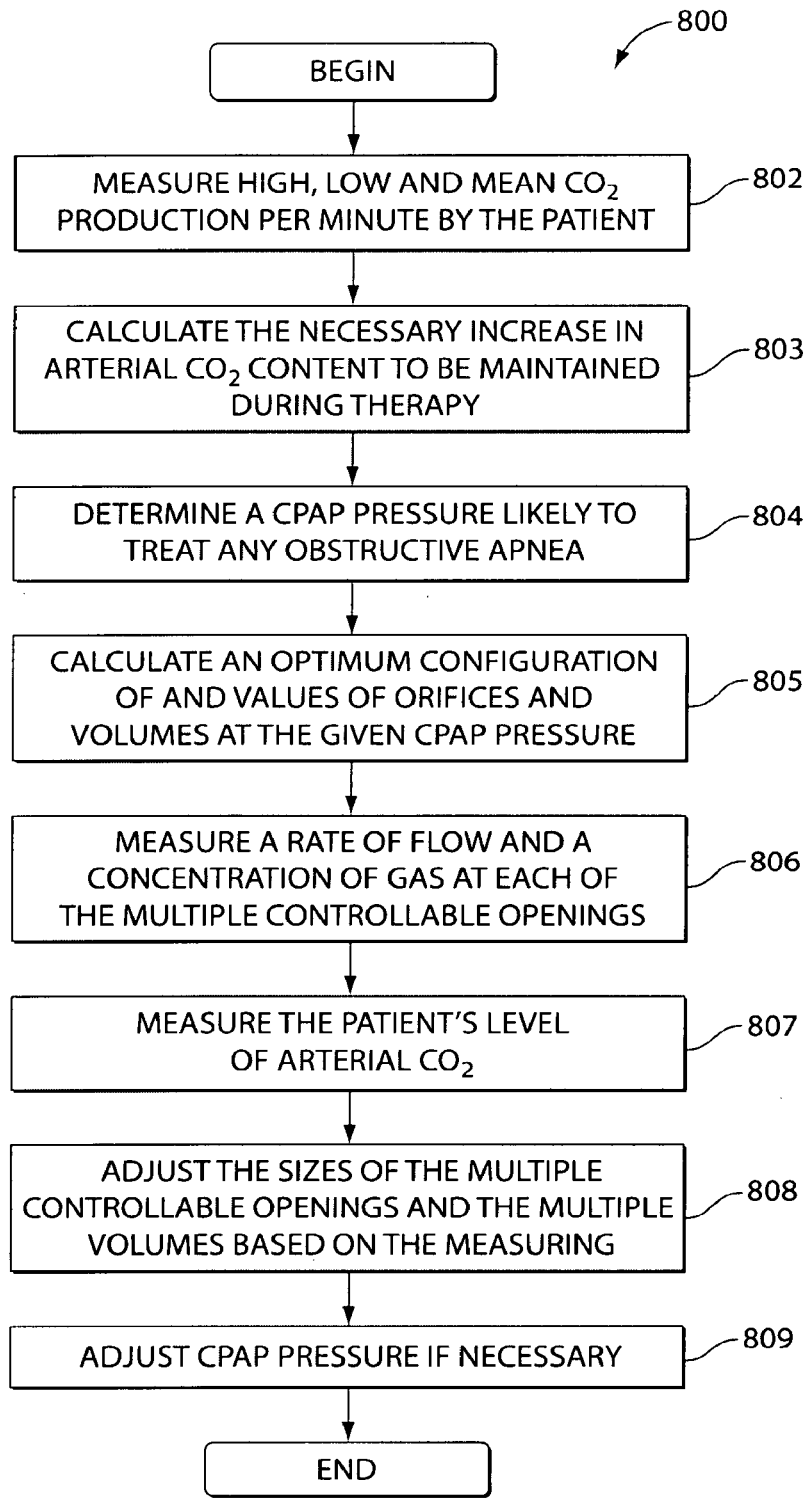
FIG. 8 is a flow chart illustrating an exemplary method for controlling breathing of a patient, according to the present invention.
Figure 9:
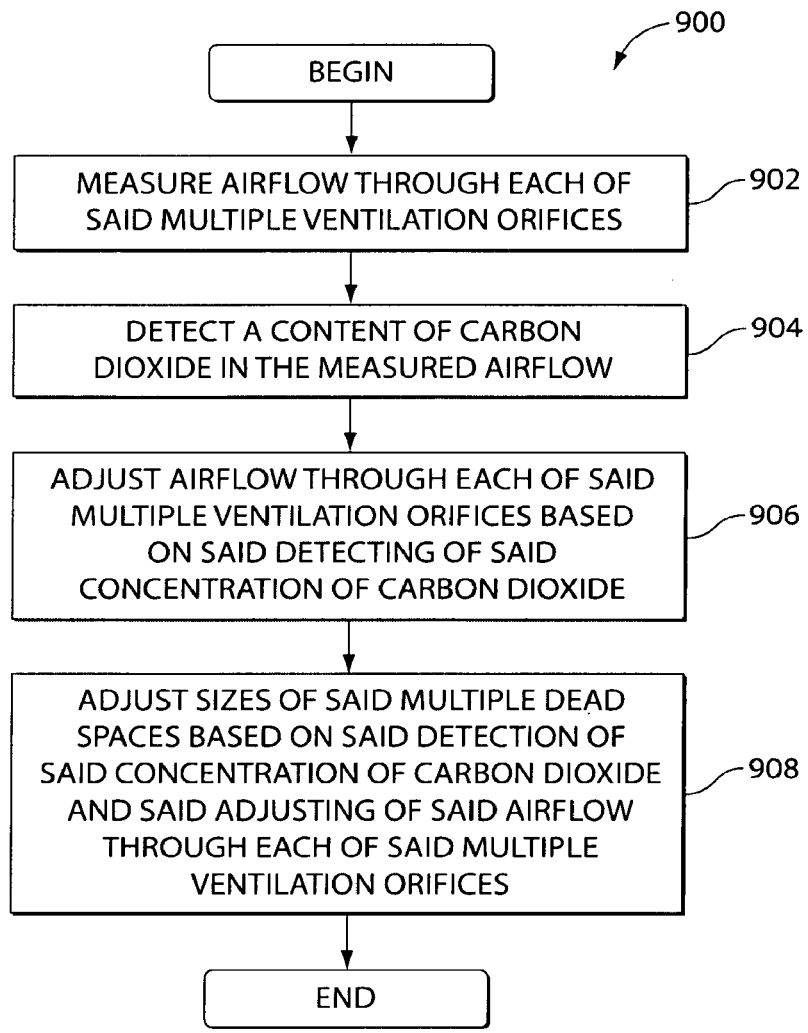
FIG. 9 is a flow chart illustrating an alternate embodiment of a method for controlling breathing of a patient, according to the present invention.

FIGS. 8 and 9 illustrate exemplary methods 800 and 900, respectively, of controlling breathing of a patient in accordance with the above discussion and using the systems shown in FIGS. 1A-2B. Referring to FIG. 8, method 800 begins with step 802. In step 802, the amount of $CO_2$ generated by the patient is determined (high, low and mean values of $CO_2$ production per minute by the patient are measured). Then, the processing proceeds to step 803, where the end-tidal $CO_2$ tracing for the night is inspected to determine the magnitude of a desired increase in the mean arterial $CO_2$ during therapy. In step 804, the optimum CPAP pressure likely to treat any existing obstructive apnea is determined. Then, in steps 805 and 806, a preliminary configuration of the system 100 is determined using the data gathered in steps 802-804. To configure the system, a computer simulation of the performance of the system under various assumptions can be used. Alternatively, empirically determined values for the orifices and volumes that are a function of the data gathered in steps 802 and 804 in addition to patient's physiological and/or demographic data can be used. In step 806, a rate of flow and concentration of gas at each of the multiple controllable openings is measured. In step 807, patient's arterial $CO_2$ level is measured. Then, in steps 808-809 the sizes of the orifices, volumes, and optionally CPAP pressure are adjusted. Steps 808-809 can be repeated until a specific configuration of orifices, volumes and CPAP pressure is reached.

Referring to FIG. 9, method 900 begins with step 902, where airflow through each of the multiple ventilation orifices 131, 133, 135 is measured. In step 904, the content of $CO_2$ in the airflow, measured in step 902, is determined. The method then proceeds to step 906. In step 906, the airflow is adjusted through each of the multiple ventilation orifices based on the detecting, performed in step 904. In step 908, the sizes of the deadspace volumes are adjusted also based on the detecting of step 904 as well as the adjustment of the multiple ventilation orifices performed in step 906.

As can be understood by one having ordinary skill in the art, the above methods can be applied in a laboratory setting, a hospital, a clinic, at patient's home, or any other facility.

FIG. 3 illustrates a relationship 300 between multiple deadspace volumes 111, 113, 115 and multiple orifices 131, 133, 135, which permits an extensive modeling of the rate of excretion of $CO_2$ ($\overset{\circ}{V}_{CO_2}$) by the patient with respect to various rates of ventilation ($\overset{\circ}{V}_E$). In an embodiment, the present invention includes two deadspace volumes 111 and 113 and three ventilation orifices 131, 133, 135 that cause various changes in the slope of FIG. 3.

Figure 4:
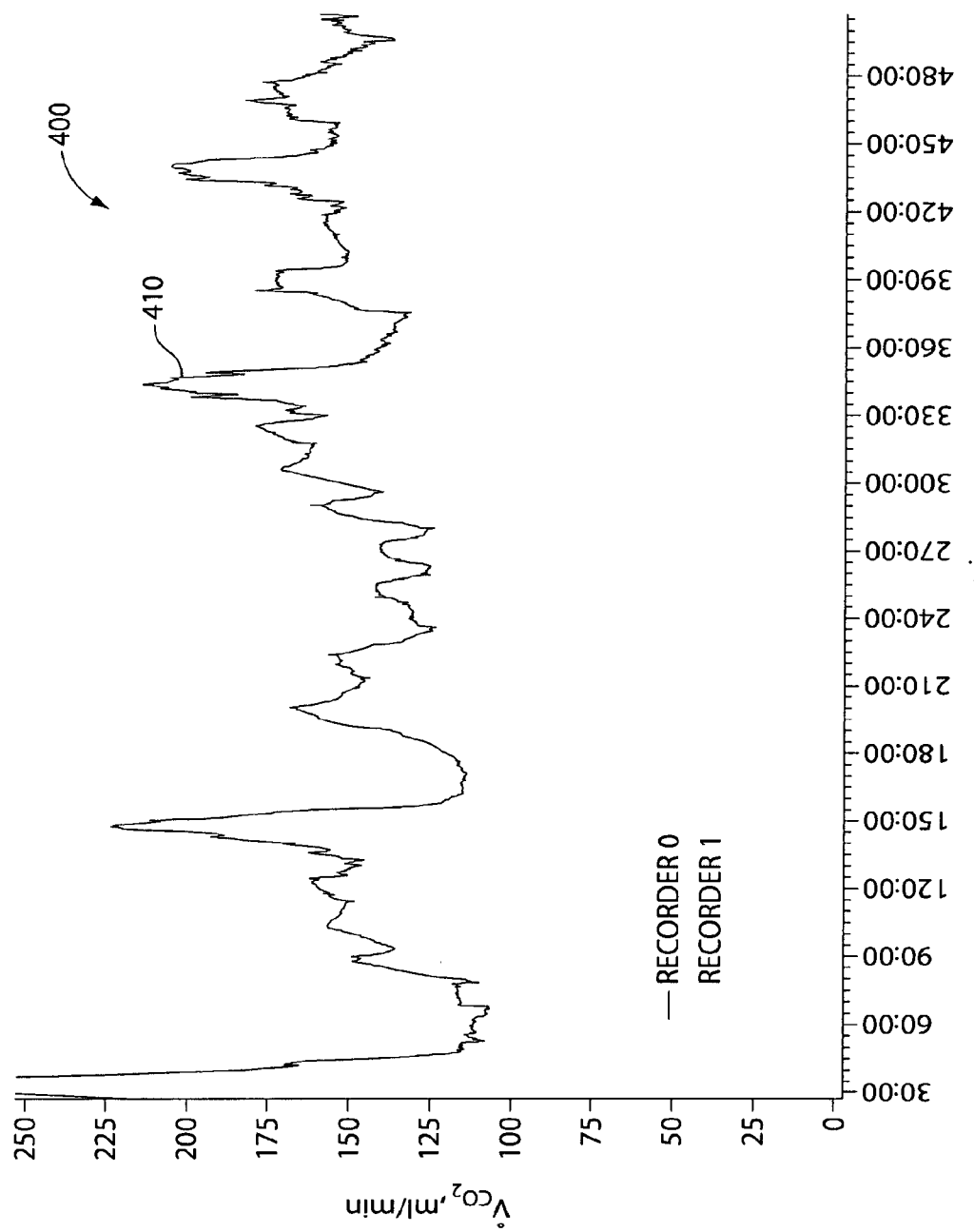
FIG. 4 is a graphical representation of a typical $CO_2$ excretion by the patient during a night.
Figure 5:
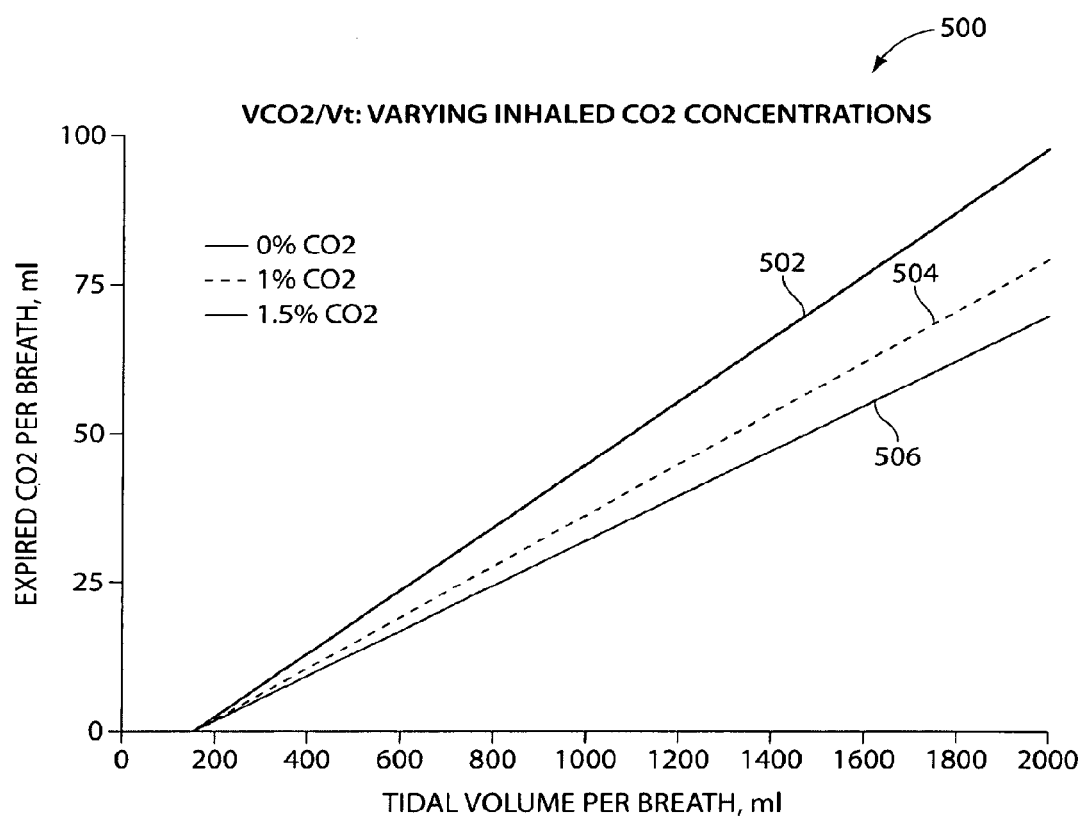
FIG. 5 is a graphical representation of a relationship between depth of breathing (i.e., tidal volume) and $CO_2$ excretion during a single breath by the patient using conventional methods and systems for controlling breathing a patient.

In FIG. 3, curve 302 represents a nightly $CO_2$ excretion profile of a patient which is overlaid on the plot to illustrate the range of likely $CO_2$ excretion rates by the patient. Referring to FIG. 4, the horizontal axis of the plot represents time in minutes and the vertical axis represents a rate of production of $CO_2$ by a patient per minute, as measure in milliliters per minute (ml/min). Referring back to FIG. 3, the horizontal axis represents patient's rate of ventilation $\overset{\circ}{V}$ measured in ml/min, and the vertical axis represents the rate of excretion of $CO_2$ $\overset{\circ}{V}$ by the patient in ml/min when the present invention's system is used. A typical relationship between these two quantities, when the present invention's system is not used, is defined as follows:

$$\overset{\circ}{V}_{CO_2} = (\overset{\circ}{V}_E - \overset{\circ}{V}_D) * (F_{ACO_2} - F_{ICO_2}) \quad (1)$$

where $\overset{\circ}{V}_D$ is equal to the sum of the physiological and artificially added volumes of deadspace multiplied by the respiratory frequency; $\overset{\circ}{V}_E$ is equal to the total volume of air inspired and expired during each breath multiplied by the respiratory frequency, $F_{ACO_2}$ is the partial pressure of dissolved $CO_2$ in arterial blood divided by an ambient air pressure; $F_{ICO_2}$ is a fractional concentration of $CO_2$ in the air inspired by the patient. The function described in equation (1) is represented by a straight line that intersects a horizontal axis above zero.

Referring back to FIG. 3, the curve 320 describes a relationship between $\overset{\circ}{V}_E$ and $\overset{\circ}{V}$ according to the present invention, and includes the following segments: hypoventilatory traverse segment 304, first respiratory plateau segment 306, eucapnic traverse segment 308, second respiratory plateau segment 310, and hyperventilatory traverse segment 312. Each segment has a specific slope and length defined by the number and size of deadspace volumes and orifices placed in the respiratory conduit as well as volume of $CO_2$ flowing through the deadspace volumes and orifices. Thus, the number of segments varies with the number of deadspace volumes and orifices in the conduit.

As shown in FIG. 3, the hypoventilatory traverse segment 304 is caused by the placement of the first orifice in the respiratory conduit. The slope of the segment illustrates a normal relationship between breathing and $CO_2$ excretion described in equation (1) until a saturation point is reached. The saturation point that corresponds to a maximum rate of $CO_2$ flow through the first orifice is represented as the junction of the segment 304 and segment 306.

This hypoventilatory traverse describes a relationship between ventilation and $CO_2$ excretion while the patient is hypoventilating. At values of $\overset{\circ}{V}_{CO_2}$ below he estimated minimum sleeping level, the relationship between $\overset{\circ}{V}_E$ and $\overset{\circ}{V}_{CO_2}$ is substantially unchanged from the normal physiological relationship. One of the destabilizing elements in unstable respiratory syndromes is the rapid accumulation of blood $CO_2$ during epochs of hypoventilation. Due to the inherent time delay in executing the control loop, overshoot is inevitable when this happens and the accumulation will quickly result in blood $CO_2$ levels that are substantially above normal. The system described herein substantially minimizes any $CO_2$ build-up and provides sufficient ventilation to expel all exhaled $CO_2$ during hypoventilation immediately through the orifices. The size of the first orifice together with the configuration of the other orifices and deadspace volumes as well as patient's respiratory parameters determines the value at which the relationship between $\overset{\circ}{V}_{CO_2}$ and $\overset{\circ}{V}_E$ begins to depart from normal values. The first orifice is sufficiently large to place this first inflection point in the curve 320 at or just below the minimum expected sleeping $\overset{\circ}{V}_{CO_2}$ (See, FIG. 3).

The first respiratory plateau segment 306 represents an effect of placing a first deadspace volume in the respiratory conduit. Once the first orifice reaches the saturation point, it does not matter how much the patient increases ventilation until such increase overcomes the first deadspace volume by pushing expired $CO_2$ beyond the first deadspace volume and past the second orifice. Hence, increases in ventilation do not result in any additional $CO_2$ excretion until this point is reached. The rate of ventilation at which the first deadspace is overcome and $CO_2$ can flow from the second orifice is defined at the junction of the segment 306 and segment 308.

This respiratory plateau includes a zone where increased respiration above the first inflection point in the curve results in virtually no increase in $\overset{\circ}{V}_{CO_2}$. This segment has a slope substantially near zero. The existence of this respiratory plateau is due to the fact that the first deadspace volume is larger than the volume of gas that can be expelled through first orifice during the duration of a typical breath. The remaining volume of $CO_2$ is re-inhaled. Any additional $CO_2$ volume within the first deadspace volume does not result in increased levels of excreted $CO_2$. The onset of an unstable respiratory cycle often commences with a progressive narrowing of the airway, resulting in decreasing $\overset{\circ}{V}_E$. The instability may further develop if decreases in $\overset{\circ}{V}_E$ are accompanied by proportional decreases in $\overset{\circ}{V}_{CO_2}$. This gives rise to a build-up of $CO_2$ in the blood sufficiently rapid to cause "overshoot" before the brain can respond to the build-up. The existence of the first respiratory plateau serves to maintain $CO_2$ excretion at a steady level in the face of substantial decreases in $\overset{\circ}{V}_E$, thus, avoiding a rapid $CO_2$ build-up and preventing substantial "overshoot" as the brain has time to respond to the decrease in ventilation. When recovering from an epoch of low or no ventilation, the first respiratory plateau prevents the increase in $CO_2$ excretion from increasing proportionally to the increase in ventilation. In a similar fashion, this places an obstacle in front of excessive $CO_2$ blow-off that poses the possibility of "undershoot."

The first respiratory plateau segment 306 also permits the clinician to specify a mean arterial level of $CO_2$ for the patient during sleep. Since affected patients are typically at least slightly hypocapnic (i.e., having lower than normal $CO_2$ in arterial blood), it is desirable to reset their sleeping $CO_2$ levels to a value that is closer to normal. The length of the first respiratory plateau segment 306 determines blood $CO_2$ during therapy. Further, since the segment 306 is generated as a result of existence of the first deadspace volume in the mixing device, increasing the size of the first deadspace volume will raise blood $CO_2$ levels. The amount by which any such increase in volume will raise blood $CO_2$ levels can be calculated based on the patient's collected data.

The eucapnic traverse segment 308 represents placement of a second orifice in the respiratory conduit. Until this orifice is saturated (i.e., the point at which the concentration of $CO_2$ in the air flowing from the orifice reaches a maximum), increases in the rate of ventilation $\overset{\circ}{V}$ result in increases in the rate of $CO_2$ excretion ($\overset{\circ}{V}_{CO_2}$). The saturation point of the second orifice is defined at the junction of the segment 308 and 310.

Further, segment 308 represents the relationship between $\overset{\circ}{V}$ and $\overset{\circ}{V}_{CO_2}$ in the range of expected sleeping $\overset{\circ}{V}_{CO_2}$. Segment 308 is a straight line having a slope that is substantially less than that of the hypoventilatory traverse segment 304. The slope of this relationship as it passes through the actual rate of $CO_2$ production by the patient at a given time establishes the conditions for respiratory stability. The slope is a variable in the relationship describing a closed-loop gain in the respiratory control feedback loop. Since the gain in the control becomes excessive in unstable respiratory syndromes, reducing the slope of the segment 308 in an immediate vicinity of a point where $CO_2$ production and excretion match (i.e., eucapnia) stabilizes respiration.

The slope of the eucapnic traverse segment 308 is governed by multiple variables, such as the first and second deadspace volumes and sizes of the first and second ventilatory orifices. The slope of segment 308 becomes shallower when larger deadspace volumes are used and where the saturation points of the first and second orifices are closer together. The range of $\overset{\circ}{V}$ traversed is also determined by the size of the second orifice 133. The measurement of patient's sleeping $\overset{\circ}{V}_{CO_2}$ permits setting the first respiratory plateau segment 306 at the highest appropriate $\overset{\circ}{V}_{CO_2}$ level and making the length of the eucapnic traverse segment 308 as short as possible. This achieves a shallow slope of the segment 308.

The second respiratory plateau segment 310 is similar to the first respiratory plateau segment 306, however, segment 310 represents placement of a second deadspace volume in the respiratory conduit. The effects produced are similar to those discussed above with respect to segment 306. The saturation point of the second deadspace volume is defined at the junction of the segment 310 and 312.

The second respiratory plateau segment 310 is disposed above the highest expected sleeping value of $\overset{\circ}{V}$ and functions in a manner similar to that of the first respiratory plateau segment 306. It is also a line segment with a nearly zero slope and constitutes a zone where changes in $\overset{\circ}{V}_E$ result in little or no change in $\overset{\circ}{V}$. The length of the second respiratory plateau segment 310 is determined by the volume of the second deadspace. It inhibits $CO_2$ excretion during hyperventilation, as sharp increases in ventilation result in little or no increase in $\overset{\circ}{V}$ The first and second respiratory plateaus segments 306, 310 provide a powerful "ventilatory clamp." While $\overset{\circ}{V}$ can vary outside of the zone determined by the two plateaus 306, 310, it will do so in response to a very strong stimulus, e.g., a need to excrete $CO_2$ rapidly after a prolonged obstructive apnea.

The hyperventilatory traverse segment 312 represents placement of an "escape" valve or a third orifice in the respiratory conduit. The third orifice is larger than the other two orifices. This allows escape of $CO_2$ after saturation of the first and second orifices and deadspace volumes. As can be understood by one having ordinary skill in the art, other configurations of orifices and deadspace volumes are possible, thus, resulting in a different graphical representation.

The hyperventilatory traverse segment 312 serves as a safety precaution in the event that it will be necessary to excrete $CO_2$ at a higher than expected rate, e.g., after a lengthy obstructive breathing event. Such excretion generates vigorous breathing at rates that are twice or more the normal rate of ventilation required to achieve such $\overset{\circ}{V}$ levels. Without the hyperventilatory traverse there is a risk of developing at least temporary respiratory acidosis under some circumstances. The hyperventilatory traverse is created by the third orifice 135, which can be larger than orifices 131 and 133. The size of the orifice 135 is determined by the ability of the CPAP machine 130 to maintain pressure at maximum flow rates likely to be encountered during treatment. In an embodiment, the orifice 135 is made as large as possible without overtaxing the CPAP machine.

Figure 6:
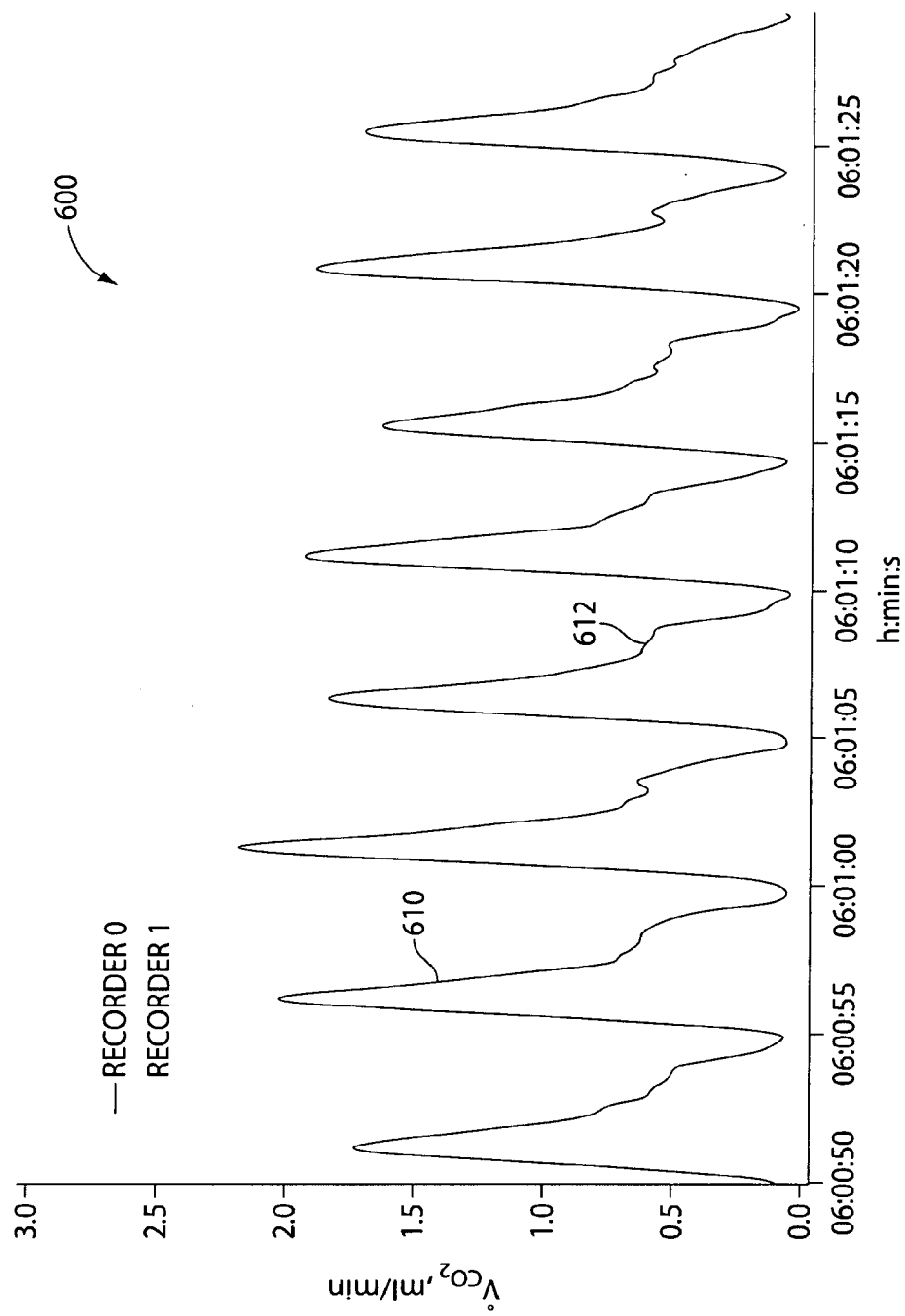
FIG. 6 is a graphical representation of a rate of $CO_2$ escaping from the apparatus for controlling breathing of a patient over the course of eight typical breaths, according to the present invention.

FIG. 6 illustrates a tracing 600 the concentration of $CO_2$ in the air flowing out of all of the orifices of the system together over the course of eight breaths. In this tracing the system is correctly adjusted and a characteristic "hip" 612 develops in the waveform. The existence of this hip is due to the elimination of all exhaled $CO_2$ from the second deadspace at a point in the breathing cycle and thus a cessation of all $CO_2$ flow through the second orifice. Since significant $CO_2$ remains in the first deadspace and in fact the first orifice remains saturated for a further period of time, the flow of $CO_2$ remains briefly at the level of the hip until the first deadspace is fully exhausted. The lack of a hip is an indication that the first orifice is too large and the emergence of a second hip is an indication that the first and second orifices taken together are too small. Thus, the system may be tunable with reference to the morphology of this waveform.

Figure 10:
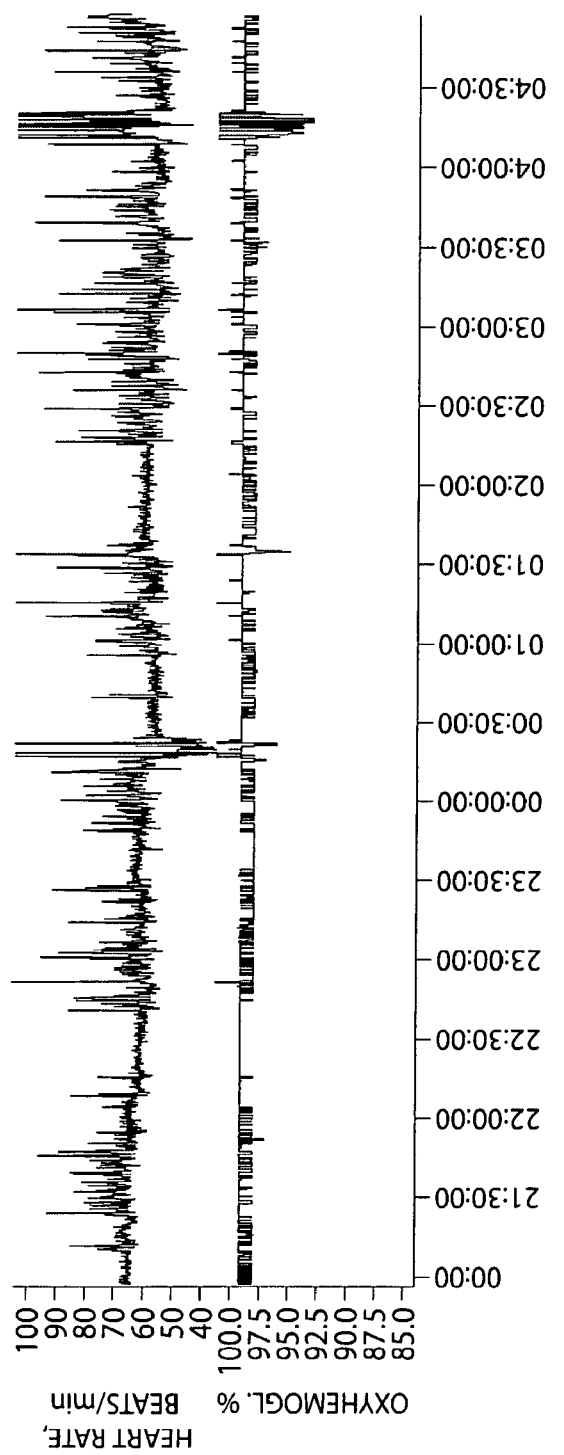
FIG. 10 is a series of tracings showing heart rate and blood oxygen saturation through the night for a patient using conventional methods and systems for controlling breathing.
Figure 11:
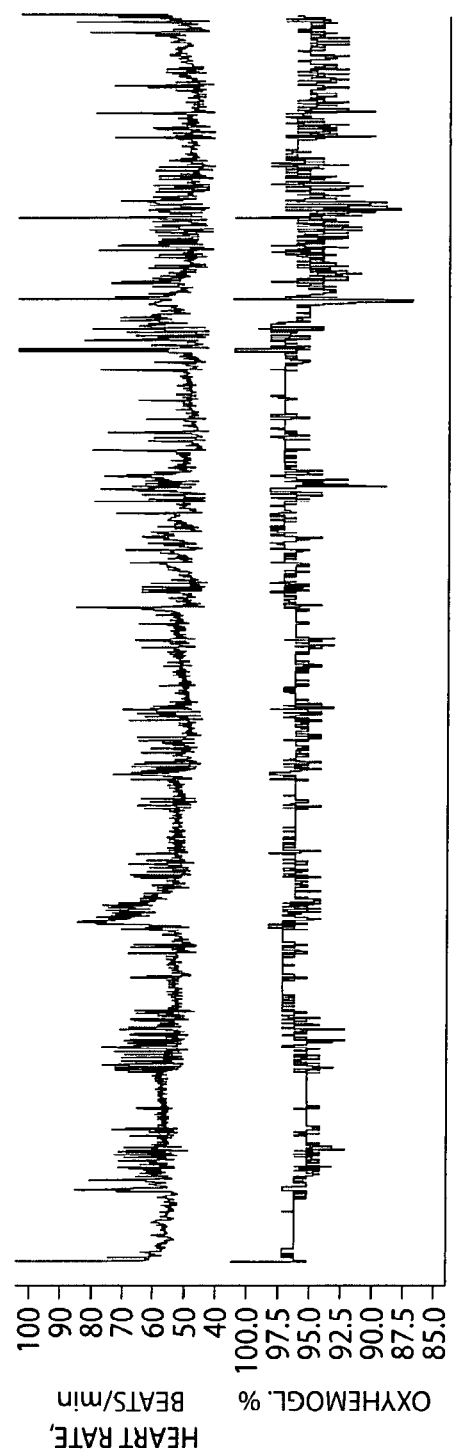
FIG. 11 is a series of tracings showing heart rate and blood oxygen saturation through the night for a patient using a conventional pressurized air supply machine alone.

FIGS. 10-11 illustrate tracings of a heart rate (respective upper portions of the figures) and blood oxygen saturation levels (respective lower portions of the figures) for a patient during a night. The segments of the heart rate tracings containing dense spikes indicate disturbed or fragmented sleep due to frequent arousals originating from a respiratory anomaly. The segments of the heart rate tracings not containing frequent spikes indicate restful or consolidated sleep. FIGS. 10 and 11 illustrate that the affected patient actually gets very few and short periods of consolidated sleep during the night using conventional methods and systems for controlling breathing.

Figure 12:
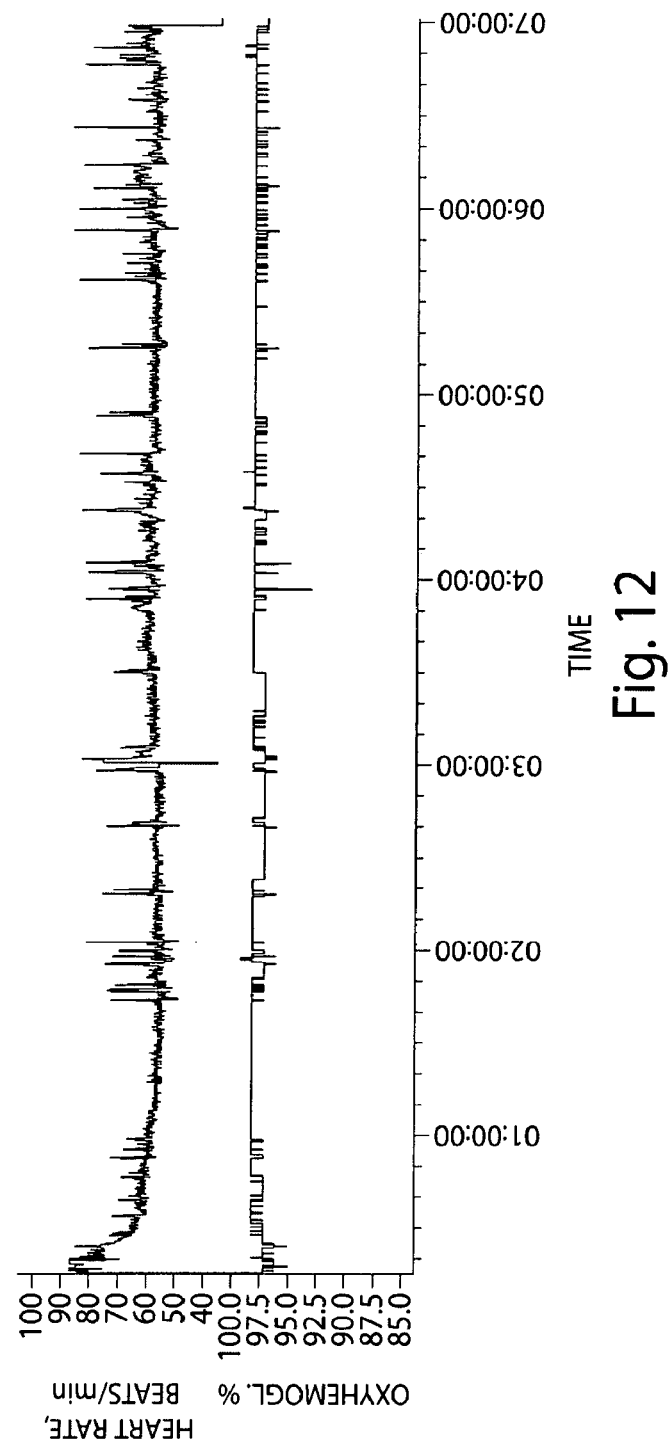
FIG. 12 is a series of tracings showing heart rate and blood oxygen saturation through the night, according the present invention.

FIG. 12 illustrates tracings of heart rate and blood oxygen saturation using the systems and methods discussed in FIGS. 1A-9. The device substantially resolved the frequent arousals, permitting long periods of restful, consolidated sleep. This results in an improvement of symptoms and is indicated by the existence of far fewer spikes in the heart rate tracings, as well as a virtually fixed oxygen tracing. Further, the system described herein has increased the patient's blood oxygen saturation to a level nearly the same as that in FIG. 10, where three liters per minute of supplemental oxygen were being given. The oxygen levels indicated in FIG. 12 were achieved using only the system and no supplemental oxygen. These data indicate that the therapeutic system effectively and reliably eliminates arousals caused by breathing anomalies while maintaining very favorable blood oxygen levels. This provides substantial symptomatic relief to affected patients.

In an exemplary setting, the present invention allows for 2-2.5% improvement in oxyhemoglobin saturation in a patient as compared to free breathing of ambient air. Since the oxyhemoglobin saturation curve is flat at its high end, this represents an important increase in available oxygen at the perfused tissues. Further, the present invention potentially obviates a need for supplemental oxygen in a number of medical settings. Also, by increasing oxygenation the present invention may reduce the sensitivity of the peripheral chemoreceptor, which causes most periodic breathing syndromes.

The present invention forces an increase in the depth of breathing and, thus, the overall rate of ventilation, since the first orifice is configured to saturate at a level that is insufficient to permit excretion of all $CO_2$ being produced by the patient. The patient breathes deeply enough to push $CO_2$ through the first deadspace volume, so that $CO_2$ exits the device through at least the second orifice. By the time patient's inspiratory interval commences, the exhaled gas in various deadspace volumes has been replaced with air and, thus, the concentration of oxygen in the inspired air is only slightly lower than that in the ambient air. Taking the two things together, the increase in breathing more than offsets the slight decline in oxygen content of inspired air ($F_{IO_2}$) to produce greater oxygen transport in the lungs. Conventional single proximal deadspace produces a decrease in $F_{IO_2}$ that more closely matches or exceeds the increase in ventilation and therefore, a frequent need for supplemental oxygen. This is because the deadspace is filled with exhaled breath and remains filled until inhalation commences. Conventional single distal deadspace neither increases ventilation nor decreases $F_{IO_2}$ versus normal breathing, thus, there should be no change in oxygen saturation.

The present invention, as described with respect to FIGS. 1A-12, can be used in the following areas:

1. Recovery from carbon monoxide poisoning. The systems and methods of the present invention speed up the rate of clearance of CO by three to five times relative to the conventionally available methods (e.g., giving oxygen).
2. Prevention of hypocapnia during birth. Hyperventilation by the delivering mother is very common and cuts oxygen supply to the fetus substantially due to a sharp drop in $CO_2$. Low $CO_2$, or hypocapnia, inhibits oxygen transport in many ways. The present invention improves oxygen flow to the fetus during delivery.
3. Recovery from altitude sickness/mountain climbing. The present invention systems and methods without use of the CPAP machine allows quick recovery from this condition.
4. Recovery from ventilator dependency. It is often difficult to wean patients from ventilator dependency, which is a cause of death in a critical care setting. The present invention stimulates breathing and increases oxygenation of the patient allowing the patient to quickly recover.
5. Recovery from anesthesia. This is similar to the recovery from ventilator dependency.
6. Obviating the use of supplemental oxygen in certain chronic lung diseases. Chronic obstructive pulmonary disease is very common and requires expensive oxygen therapy. However, with the present invention there is no need to use such oxygen therapy.
7. As can be understood by one having ordinary skill in the art, other uses of the present invention's systems and methods are possible.

Example embodiments of the methods, circuits, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A method of controlling breathing of a patient, wherein air is supplied to the patient using a patient interface device coupled to a pressurized air supply device using a respiratory conduit that includes first and second controllable openings and first and second volume connectors configured as partial dead space volumes positioned along the length of the respiratory conduit, the method comprising:

determining a rate of production of carbon dioxide generated by the patient;

measuring a rate of flow and a concentration of carbon dioxide at each of the controllable openings;

adjusting sizes of each of the first and second controllable openings based on the measuring to control a rate of excretion of carbon dioxide from the respiratory conduit to the ambient air and a concentration of carbon dioxide in blood of the patient, wherein the adjusting is configured to allow a range of amounts of carbon dioxide excreted from the respiratory conduit to the ambient air to be substantially equal to a range of production of carbon dioxide by the patient during a period of time; and adjusting sizes of at least one of the volume connectors based on at least one of the determining and the measuring;

adjusting the first controllable opening to allow an escape of an amount of carbon dioxide to the ambient air that is lower than or equal to the amount of carbon dioxide produced by the patient during a period of time;

adjusting the second controllable opening to allow an escape of an amount of carbon dioxide to the ambient air that is based upon i) the amount of carbon dioxide allowed to escape from the first controllable opening, and ii) a maximum total amount of carbon dioxide produced by the patient during a period of time; and wherein air supplied to the patient includes a mixture of air supplied by the air supply device and carbon dioxide generated by the patient.

2. The method according to claim 1, further comprising:

determining an increase in a pressure of carbon dioxide in the arterial blood of the patient, wherein the determining includes:

measuring the pressure of carbon dioxide contained in the arterial blood of the patient using time-based monitoring selected from the group consisting of: end-tidal carbon dioxide monitoring, transcutaneous carbon dioxide monitoring, and arterial blood carbon dioxide analysis; and calculating a desired change in pressure of the carbon dioxide in the arterial blood of the patient based on the measuring.

3. The method according to claim 1, further comprising:

modifying sizes of the controllable openings and the volume connectors, wherein the modifying includes:

monitoring an amount of the carbon dioxide escaping from each of the controllable openings and the volume connectors; and measuring a rate of flow and a concentration of carbon dioxide at each of the controllable openings;

adjusting sizes of the volume connectors based on at least one of the determining and the measuring;

wherein carbon dioxide supplied to the patient is a mixture of carbon dioxide supplied by the supply device and carbon dioxide produced by the patient during breathing.

4. The method according to claim 3, wherein the modifying is performed as a result of a collapse of the patient breathing airway.

5. The method according to claim 4, further comprising:

adjusting pressure of air supplied to the patient during breathing until the patient breathing airway is no longer collapsed.

6. The method according to claim 1, wherein the determining further comprises estimating the amount of the carbon dioxide produced by the patient using at least one characteristic selected from a group consisting of: age, gender, body mass, percent lean body mass and the partial pressure of the carbon dioxide in the arterial blood of the patient.

7. The method according to claim 1, wherein the determining further comprises determining the sizes of the controllable openings and volume connectors using a predetermined simulation of normal breathing of the patient.

8. The method according claim 7, wherein the determining further comprises:
calculating a minimum, a maximum, and a mean amount of carbon dioxide escaping from each of the controllable openings during breathing; and
based on the calculating, adjusting a size of at least one of the controllable openings and at least one size of each of the volume connectors.

9. The method according to claim 1, wherein a rate of air flow through one of the controllable openings is based on a rate of flow through at least one other one of the controllable openings.

10. The method according to claim 1, wherein a rate of flow of a carbon dioxide through the controllable openings is calculated based on an expected rate of production of the carbon dioxide by the patient, expected respiration rate of the patient, expected depth of respiration by the patient, and an expected concentration of the carbon dioxide in the air expired by the patient.

11. The method according to claim 1, wherein a volume of expired carbon dioxide by the patient that is re-breathed by the patient is continuously adjusted based on a volume of carbon dioxide allowed to escape from the multiple controllable openings and a volume of carbon dioxide contained in the multiple volume connectors.

12. A method for controlling flow of carbon dioxide to a patient during breathing, using a pressurized air supply device coupled to a patient interface device placed on the patient, the patient interface device is coupled to a carbon dioxide mixing device, which is coupled to the pressurized air supply device, the carbon dioxide mixing device includes first and second ventilation orifices in communication with the ambient air that are interchangeably connected with multiple dead spaces, wherein the first and second ventilation orifices control supply of carbon dioxide to the patient and volume of carbon dioxide in the multiple dead spaces, the method comprising:
measuring airflow through each of the ventilation orifices;
detecting a content of carbon dioxide in the measured airflow;
adjusting airflow through each of the ventilation orifices based on the detecting of the concentration of carbon dioxide to control a rate of excretion of carbon dioxide from the respiratory conduit to the ambient air and a concentration of carbon dioxide in blood of the patient wherein the adjusting allows a range of amounts of carbon dioxide excreted from the respiratory conduit to the ambient air to be substantially equal to a range of production of carbon dioxide by the patient during a period of time;
adjusting the first ventilation orifice to allow an escape of an amount of carbon dioxide to the ambient air that is lower than or equal to the amount of carbon dioxide produced by the patient during a period of time;
adjusting the second ventilation orifice to allow an escape of an amount of carbon dioxide to the ambient air that is based upon i) the amount of carbon dioxide allowed to escape from the first ventilation orifice, and ii) a maximum total amount of carbon dioxide produced by the patient during a period of time; and
adjusting sizes of the multiple dead spaces based on the detection of the concentration of carbon dioxide and the adjusting of the airflow through each of the multiple ventilation orifices.

13. The method according to claim 12, further comprising:
adjusting sizes of the dead spaces and the ventilation orifices based on a relationship between CO2 and E, wherein CO2 is a rate of excretion of carbon dioxide by the patient per minute; E is a total rate of ventilation per minute by the patient;
wherein a curve representing the relationship between CO2 and E contains at least two discontinuities;
the discontinuities are determined using the lengths of a hypoventilatory traverse segment caused by a placement of at least the first ventilation orifice in the carbon dioxide mixing device;
a first respiratory plateau segment caused by a placement of at least the first dead space in the carbon dioxide mixing device;
a eucapnic traverse segment caused by a placement of at least the second ventilation orifice in the carbon dioxide mixing device;
a second respiratory plateau segment caused by a placement of at least the second dead space in the carbon dioxide mixing device; and
a hyperventilatory traverse segment caused by a placement of at least a third ventilation orifice in the carbon dioxide mixing device.

14. The method according to claim 13, wherein the hypoventilatory traverse segment has a slope defined by a relationship between volume of air breathed by the patient during a breathing interval and an amount of carbon dioxide exhaled by the patient in the breathing interval.

15. The method according to claim 13, wherein during the eucapnic traverse segment, an additional volume of carbon dioxide escapes from at least the second ventilation orifice, wherein the additional volume is determined based on the volume of carbon dioxide that escaped from at least the first ventilation orifice.

16. The method according to claim 13, wherein during the hyperventilatory traverse segment, an additional volume of carbon dioxide escapes from at least the third ventilation orifice, wherein the additional volume is determined based on a volume of carbon dioxide that escaped from at least first and second ventilation orifices.

17. The method according to claim 12, further comprising determining a target mean arterial concentration of carbon dioxide based on the adjusting sizes step.

18. The method according to claim 12, wherein the adjusting sizes step is automatic.

19. The method according to claim 12, wherein the adjusting sizes step is manual.

20. A method for controlling breathing of a patient using a respiratory conduit configured to be coupled to a patient interface device and a pressurized air generating device, wherein the conduit includes at least three air flow control devices positioned between the patient interface device and the pressurized air generating device and at least two volumes that function as partial dead spaces, wherein a first volume is positioned between a first air flow device and a second air flow device, and a second volume is positioned between the second air flow device and a third air flow device, the method comprising:
receiving carbon dioxide in the conduit, wherein the carbon dioxide originates from an expiratory breath of the patient; and allowing escape of carbon dioxide from the at least three air flow control devices to ambient air in a range substantially equal to a range of carbon dioxide produced by the patient during a period of time;

wherein a portion of the received carbon dioxide escapes from the first air flow control device to the ambient air and another portion of the received carbon dioxide travels through the first volume to the second air flow control device;

wherein a part of the another portion of the received carbon dioxide escapes from the second air flow control device to the ambient air and another part of the another portion of the received carbon dioxide travels through the second volume to the third air flow control device; and wherein the another part of the another portion of the received carbon dioxide escapes from the third air flow control device to the ambient air.

* * * * *